US008216568B2

(12) United States Patent
Plaut et al.

(10) Patent No.: US 8,216,568 B2
(45) Date of Patent: *Jul. 10, 2012

(54) COMBINATION THERAPY WITH IGA1 PROTEASES

(75) Inventors: Andrew G. Plaut, Lexington, MA (US); Jiazhou Qiu, Westborough, MA (US)

(73) Assignee: Tufts Medical Center, Boston, MA (US)

( * ) Notice: Subject to any disclaimer, the term of this patent is extended or adjusted under 35 U.S.C. 154(b) by 376 days.

This patent is subject to a terminal disclaimer.

(21) Appl. No.: 12/177,125

(22) Filed: Jul. 21, 2008

(65) Prior Publication Data

US 2009/0041746 A1    Feb. 12, 2009

Related U.S. Application Data

(63) Continuation of application No. 10/921,676, filed on Aug. 19, 2004, now Pat. No. 7,407,653, which is a continuation-in-part of application No. PCT/US2004/006615, filed on Mar. 5, 2004.

(60) Provisional application No. 60/453,055, filed on Mar. 7, 2003.

(51) Int. Cl.
*A61K 38/48* (2006.01)
(52) U.S. Cl. .................................. 424/94.64
(58) Field of Classification Search ............... 424/94.64
See application file for complete search history.

(56) References Cited

U.S. PATENT DOCUMENTS 7,407,653 B2    8/2008    Plaut et al.

FOREIGN PATENT DOCUMENTS

WO    WO 90/11367    10/1990
WO    WO 2004/096157 A2    11/2004

OTHER PUBLICATIONS

Poulsen et al, J Bacteriol. May 1992;174(9):2913-21. A comparative genetic study of serologically distinct Haemophilus influenzae type 1 immunoglobulin A1 proteases.*
U.S. Appl. No. 60/453,055, filed Mar. 7, 2003, Plaut et al.
Appel et al., "The IgA nephropathy treatment dilemma" *Kidney Int.* 69(11):1939-1944 (2006) Review.
Ballardie, "IgA nephropathy treatment 25 years on: can we halt progression? The evidence base" *Nephrol. Dial Transplant* 19(5):1041-1046 (2004).
Barratt et al., "IgA nephropathy" *J. Am. Soc. Nephrol.* 16:2088-2097 (2005).
Barratt et al., "Immunopathogenesis of IgAN" *Semin. Immunopathol.* 29:427-443 (2007).
Coppo et al., "Aberrant glycosylation in IgA nephropathy (IgAN)" *Kidney Int.* 65(5):1544-1547 (2004).
Definition: "focal glomerulonephritis" In: Stedman's medical dictionary Ed 26 1995 pp. 727.
Galye et al., "Identification of regions in interleukin-1 alpha important for activity" *J. Biol. Chem.* 268(29):22105-22111 (1993).
Gesualdo et al., "Enzymolysis of glomerular immune deposits in vivo with dextranase/protease ameliorates proteinuria, hematuria, and mesangial proliferation in murine experimental IgA nephropathy" *J. Clin. Invest.* 86(3):715-722 (1990).
Grundy et al., "Localization of the cleavage site specificity determinant of Haemophilus influenza immunoglobulin A1 protease genes" *Infect. Immun.* 58(2):320-331 (1990).
Halter et al., "IgA protease of *Neisseria gonorrhoeae*: isolation and characterization of the gene and its extracellular product" *EMBO J.* 3(7):1595-1601 (1984).
Hsu et al., "The molecular pathogenesis and experimental therapy of IgA nephropathy: recent advances and future directions" *Curr. Mol. Med.* 1(2):183-196 (2001).
International Search Report for International Application No. PCT/US04/06615, dated Aug. 16, 2005.
Julian et al., "IgA nephropathy: an update" *Curr. Opin. Nephrol. Hypertens.* 13:171-179 (2004).
Kilian et al., "IgA1 proteases from *Haemophilus influenza, Streptococcus pneumoniae, Neisseria meningitis,* and *Streptococcus sanguis*: comparative immunochemical studies" *J. Immunol.* 124(6):5896-25600 (1980).
Kilian et al., "Pathogenic species of the genus Haemophilus and *Streptococcus pneumoniae* produce immunoglobulin A1 protease" *Infect. Immun.* 26(1):143-149 (1979).
Kobayashi et al., " IgA protease from Clostridium ramosum that cleaves IgA1 and IgA2, A2m(1): the site of cleavage and digestion of secretory IgA" *Adv. Exp. Med. Biol.* 216B:1289-12996 (1987).
Koshland et al., "Selective proteolysis of the J chain component in human polymeric immunoglobin" *J. Immunol.* 118(3):775-781 (1977).
Lamm et al., "Microbial IgA protease Removes IgA Immune Complexes from Mouse Glomeruli in Vivo: Potential Therapy for IgA Nephropathy" *Am. J. Pathol.* 172 (1): 31-36 (2008).
Launay et al., "Fcalpha receptor (CD89) mediates the development of immunoglobulin A (IgA) nephropathy (Berger's disease). Evidence for pathogenic soluble receptor-Iga complexes in patients and CD89 transgenic mice" *J. Exp. Med.* 191(11):1999-2009 (2000).
Michael et al., "Recurrent haematuria: role of renal biopsy and investigative morbidity" *Br. Med. J.* 1(6011):686-688 (1976).
Nakazawa et al., "Proteolytic enzyme treatment reduces glomerular immune deposits and proteinuria in passive Heymann nephritis" *J. Exp. Med.* 164:1973-1987 (1986).
Piesecki et al , "Immobilization of beta-galactosidase for application in organic chemistry using a chelating peptide" *Biotech. & Bioeng.* 42(2):178-184 (1993).

(Continued)

*Primary Examiner* — Sheridan Swope
(74) *Attorney, Agent, or Firm* — Choate Hall & Stewart LLP; Brenda Herschbach Jarrell

(57) ABSTRACT

The present invention discloses the use of bacterial IgA1 proteases to treat IgA1 deposition in tissue and organs. Bacterial IgA1 proteases specifically cleave IgA1 molecules and thus provide a means to specifically cleave and remove IgA1 depositions. Accordingly, therapeutic agents for the treatment of diseases characterized by IgA deposition are provided. In particular, therapeutic agents to treat IgA nephropathy, Dermatitis herpetiformis (DH), and Henoch-Schoenlein purpura (HS) are disclosed.

1 Claim, 11 Drawing Sheets

OTHER PUBLICATIONS

Rostoker et al. "High-dose immunoglobulin therapy for severe IgA nephropathy and Henoch-Schönlein purpura" *Ann. Intern. Med.* 120(6):476-484 (1994).

Smith et al., "New insights into the pathogenesis of IgA nephropathy" *Springer Semin. Immunopathol.* 477-493 (2003).

Strauss et al., "C-terminal glycine-histidine tagging of the outer membrane protein Iga beta of *Neisseria gonorrhoeae*" *FEMS Microbiol. Lett.* 127(3):249-254 (1995).

Whisstock et al., "Prediction of protein function from protein sequence and structure" *Q. Rev. Biohphys.* 36(3):307-340 (2003) Review.

Conley et al., "Selective Deposition of Immunoglobulin A1 in Immunoglobulin A Nephropathy, Anaphylactoid Purpura Nephritis, and Systemic Lupus Erythematosus", J. Clin. Invest, 66:1432-1436 (1980).

Lemercier et al., "On-column refolding of an insoluble histidine tag recombinant expolyphosphatase from Trypanosoma brucei overexpressed in *Escherichia coli*", J Chromatogr B Analyt Technol Biomed Life Sci., 786:305-309 (2003).

Mortensen et al., "Purification and Characterization of an Immunoglobulin A1 Protease from Bacteroides melaninogenicus", Infection and Immunity, 45(3):550-557 (1984).

\* cited by examiner

IgA1 Hinge Region

Amino acids 217-241

1. Clostridium Rasmosum
2. Prevotella species
3. Streptococcus pnemoniae
   Streptococcus saguis
4. Haemophilus Influenzae (1)
   Haemophilus aegyptitus
5. Ureaplasma ureatyticum
   Neisseria meningitidis (2)
   Neisseria gonorrhoeae (2)
   Haemophilus Influenzae (2)
6. Neisseria meningitidis (1)
   Neisseria gonorrhoeae (1)

Schematic diagram showing *H. influenzae* Rd IgA protease precursor contains 4 sections: signal sequence, enzyme domain, α-domain, and "helper" or β-domain. Active site of the protease is near N-terminus of the enzyme domain (arrow). Top of the diagram shows details of the protein sequence mutation. 6xHis epitope is 2 residues away from the main autocatalytic site, a site.

FIG. 5

Haemophilus influenzae Rd protein sequence

MLNKKFKLNFIALTVAYALTPYTEAALVRDDVDYQIFRDFAENKGRFSVGATNVEVRD
KNNHSLGNVLPNGIPMDFSVVDVDKRIATLINPQYVVGVKHVSNGVSELHFGNLNGN
MNNGNAKSHRDVSSEENRYFSVEKNEYPTKLNGKAVTTEDQTQKRREDYYMPRLDKF
VTEVAPIEASTASSDAGTYNDQNKYPAFVRLGSGSQFIYKKGDNYSLILNNHEVGGNNL
KLVGDAYTYGIAGTPYKVNHENNGLIGFGNSKEEHSDPKGILSQDPLTNYAVLGDSGSP
LFVYDREKGKWLFLGSYDFWAGYNKKSWQEWNIYKPEFAKTVLDKOTAGSLTGSNTQ
YNWNPTGKTSVISNGSESLNVDLFDSSQDTDSKKNNHGKSVTLRGSGTLTLNNNIDQGA
GGLFFBGDYEVKGTSDSTTWKGAGVSVADGKTVTWKVHNPKSDRLAKIGKGTLIVBGK
GENKGSLKVGDGTVILKQQADANNKVKAFSQVGIVSGRSTVVLNDDKQVDPNSIYFGF
RGGRLDANGNNLTFEHIRNDDGARLVNHNTSKITSTVTITGESLIITDPNIITPYNIDAPDE
DNPYAFRRIKDGGQLYLNLENYTYALRKGASTRSELPKNSGESNENWLYMGKTSDEA
KRNVMNHINNERMNGFNGYFGEEEGKNNGNLNVTFKGKSEQNRFLLTGTNLNGDLK
VEKGTLFLSGRPTPHARDIAGISSTKKDQHFAENNEVVVEDDWINRNFKATNINVTNNA
TLYSGRNVANITSNITASDNAKVHIGYKAGDTVCVRSDYTGYVTCTTDKLSDKALNSFN
ATNVSGNVNLSGNANFVLGKANLFGTISGTGNSQVRLTENSHWHLTGDSNVNQLNLDK
GHIHLNAQNDANKVTTYNTLTVNSLSGNGSFYYLTDLSNKQGDKVVTKSATGNFTLQ
VADKTGEPTKNELITLFDASNATRNNLNVSLVGNTVDLGAWKYKLRNVNGRYDLYNPE
VEKRNQTVDTTNITPNNIQADVPSPSNNEBIARVETPVPPAPATPSETETVAENSKQ
ESKTVEKNEQDATETTAQNGEVAEBAKPSVKANTQTNEVAQSGSETEETQTTBIKETAK
VEKBEKAKVEKDEIQEAPQMASETSPKQAKPAPKEVSTDTKVEETQVQAQPQTQSTTVA
AAEATSPNSKPAEETQPSEKTNAEPVTFVVSKNQTENTTDQPTEREKTAKVETEKTQEPP
QVASQASPKQEBQSETVQPQAVLESENVPTVNNAEEVQAQLQTQTSATVSTKQPAPENSI
NTGSATAITETABKSDKPQTETAASTEDASQHKANTVADNSVANNSESSDPKSRRRRSIS
QPQBTSABETTAASTDETTIADNSKRSKPNRRSRRSVRSEPTVTNGSDRSTVALRDLTST
NTNAVISDAMAKAQFVALNVGKAVSQHISQLEMNNEGQYNVWVSNTSMNENYSSSQY
RRFSSKSTQTQLGWDQTISNNVQLGGVFTYVRNSNNFDKASSKNTLAQVNFYSKYYAD
NHWYLGIDLGYGKFQSNLKTNHNAKFARHTAQFGLTAGKAFNLGNFGITPIVGVRYSY
LSNANFALAKDRUKVNPISVKTAFAQVDLSYTYHLGEFSVTPILSARYDTNQGSGKINVN
QYDFAYNVENQQQYNAGLKLKYHNVKLSLIGGLTKAKQAEKQKTAELKLSFSF"

Haemophilus influenzae Rd nucleotide sequence atgctaaata aaaaattcaa actcaatttt attgcgctta ctgtcgccta cgcattaacc
ccttatacag aagctgcgtt agtgagagac gatgtggatt atcaaatatt tcgtgatttt
gcagaaaata aagggagatt ttctgttggt gcaacaaatg tggaagtgag agataaaaat
aaccactctt taggcaatgt tttacctaat ggcattccga tgattgattt tagtgttgtg
gatgtagata aacgcatcgc cacattgata aatccacaat atgtagtagg tgtaaaacac
gttagtaacg gcgtgagtga actacatttt gggaacttaa atggcaatat gaataatggc
aatgctaaat cgcaccgaga tgtatcttca gaagaaaata gatattttc cgttgagaaa
aatgagtatc caactaaatt gaatggaaaa gcagtaacta ctgaagatca aactcaaaaa
cgccgtgaag actactatat gccacgtctt gataaatttg ttaccgaagt tgcaccaata
gaggcttcaa ctgcaagtag tgatgctggc acatataatg atcagaataa atatcctgct
tttgtaagac taggaagtgg tagtcaattt atttataaaa aaggagataa ttacagctta
attttaaata atcatgaggt tggaggcaat aatcttaaat tggtgggcga tgcctatacc
tatggtattg caggcacacc ttataaagta aaccacgaaa ataatggact aattggtttt
ggcaattcaa aagaggaaca cagcgatcca aaaggaatat tatctcaaga tccgcttacc
aattatgctg ttttaggcga cagtggctcc ccattatttg tatatgatag agaaaaagga
aaatggcttt ttcttgggtc ttatgattt tgggcaggtt ataacaaaaa atcttggcaa
gaatggaata tttataaacc tgaatttgca aaaactgttc tagataaaga tactgcaggt
tctttaactg gttctaacac ccaatacaat tggaatccta ctggcaaaac aagcgttatt
tctaatggtt ctgaatctct aaatgttgat ttattcgata gtagtcagga tactgactct
aagaagaaca atcacggaaa aagtgtgact cttagaggaa gtggaacgct taccttaaat
aataatatcg atcaaggcgc aggcggcttg ttctttgaag gagattatga agttaaaggc

FIG. 6B acttctgata gtaccacttg gaaaggagct ggcgtttctg ttgctgatgg aaaaacagta acgtggaaag tacataaccc gaaatctgat cgtttagcta aaatcggcaa aggaacatta attgtagaag gaaagggaga aaataaaggt tcgctaaaag tgggcgatgg tactgttatc ttaaaacaac aagctgatgc caataataaa gttaaagcct tttcacaagt aggtatagta agtggtcgct caactgttgt acttaatgat gataagcaag tagatccaaa ttccatttac tttggcttta gaggtggtcg attagatgcc aatggcaata atctcacttt tgaacatatc cgtaatattg atgatggcgc aagactagta aatcacaata ccagcaaaac ctctactgta acaattactg gggaaagtct aattacagat ccaaatacaa ttactccata taatatagac gcaccagatg aagataatcc ttatgccttt cgacggatta aagatggagg acagctctat ttaaatttgg aaaattacac ttattatgcg ttaagaaaag gtgcgagcac tcgttcagaa ttacctaaaa atagtggcga aagcaatgaa aattggctat atatgggtaa aacttccgat gaagccaaaa gaaatgtaat gaaccatatc aacaacgagc gtatgaatgg ctttaacggt tattttggcg aggaagaggg taaaaataac ggtaatctaa atgtgactttt taaaggcaaa agtgagcaaa atcgcttttt attaacaggc ggaacaaacc ttaatggcga tttaaaggtt gaaaaaggca cattattcct ttctggcaga ccaacaccgc acgcaagaga tattgcaggt atttcttcga caaaaaaaga tcaacacttt gctgaaaata atgaagtggt agtagaagat gactggatta accgcaattt taaagcaaca aatattaatg taaccaataa cgcaacccttt tattcaggtc gcaatgttgc aaacattact tcaaatatca cagcttctga taatgcaaaa gtacatattg gctataaagc aggcgatacc gtttgtgtac gttctgacta tacgggctat gtgacttgca ctactgacaa gttatccgat aaagcccttaa atagctttaa cgccaccaat gtatctggca atgtaaattt atcaggtaat gcaaactttg tcttaggcaa agctaactta ttcggcacaa ttagcggcac gggaaatagc caagtacgtt taaccgaaaa tagccattgg catttaacag gcgatagcaa tgttaatcag ttaaatttag acaaggggca tattcattta aatgcacaaa acgatgcaaa taaagtaact acatataaca cgctgactgt gaatagctta tcaggtaacg gttctttcta ttatttaact gatctttcca ataaacaagg cgacaaagtt

FIG. 6C gttgtaacta aatccgccac aggtaacttt acattacaag tggcagataa aacaggcgag cctacaaaaa atgaactcac gcttttttgat gcgtcaaatg ctacaagaaa taatttgaat gtgtcattag ttgggaatac cgttgattta ggtgcttgga aatataaatt acgtaatgtt aatggacgtt acgatttgta taacccagag gtggaaaaaa gaaatcaaac tgtcgatacg acaaatatca caacacctaa taatattcaa gctgatgtgc ctagcgtacc aagtaacaat gaagaaatag cccgtgttga aacaccagtt ccaccacctg cgcctgctac accatcagag acaactgaaa cagtggctga aaatagtaag caagaaagta aaacagtaga gaaaaacgag caagacgcaa ccgagacaac agctcaaaat ggagaagttg cagaagaagc taaaccaagt gtaaaagcta atactcaaac aaatgaagtg gctcaaagtg gaagtgaaac cgaggaaact caaacgactg aaataaaaga aacagctaaa gtagaaaaag aggaaaaggc taaagtagaa aaagatgaaa ttcaagaagc acctcaaatg gcttctgaaa cgtctccgaa acaagcaaag cctgctccta aagaagtttc aactgatacg aaagtagaag aaactcaagt tcaagctcaa ccgcaaacac aatcgacaac tgttgctgcg gcagaggcaa cttcgccaaa cagtaaacca gcggaagaaa ctcaaccaag tgaaaaaact aacgctgaac ctgtaacgcc tgtagtatca aaaaatcaaa cagaaaatac gaccgaccaa ccaacagaaa gagagaaaac ggctaaagta gaaacagaga aaactcaaga acccctcaa gtggcttctc aagcgtctcc gaaacaggaa cagtctgaaa ctgttcaacc gcaagcagtg cttgaaagtg aaaatgttcc gactgttaat aatgcagaag aagttcaagc tcaactgcaa acacaaacaa gtgcaacagt aagcactaaa caacctgcac cagagaattc aataaatact ggatctgcaa ccgcaataac agaaactgct gaaaaatccg ataaaccaca aacggaaact gcggcttcga ctgaagatgc tagtcagcat aaagcgaata ctgttgcgga taattctgta gcaaataatt cagaaagcag tgatccaaag agtagacgta gaagaagtat tagccagcct caagagactt ctgctgaaga aacaacagca gcttctactg acgaaacaac aatagctgat aattcaaaac gcagtaagcc aaatcgtaga agtagaagaa gtgttcgctc ggaaccaact gttacaaatg gcagcgatcg ttctacagta gcattgcgcg atctcacaag tacaaacaca aatgcggtaa tttctgatgc aatggcaaaa gcacaatttg ttgcattaaa tgtggggaaa gcagtttctc aacatattag ccagttagaa
atgaataacg aggggcaata taacgtttgg gtatctaata cttcaatgaa cgaaaattat
tcctcaagtc aatatcgtcg ttttagttct aaaagtacgc aaactcaact tggttgggat
caaacaatct caaacaatgt tcagttaggt ggcgtgttta cttatgttcg caatagtaac
aactttgata aggcaagcag taaaaatact ctagcacaag ttaatttcta ttctaaatat
tatgcggata atcattggta tttgggcatt gatttaggct acggcaagtt ccaaagcaac
ctaaaaacca atcataatgc gaaatttgct cgccatactg cacaatttgg tttaaccgca
ggcaaagcat ttaatcttgg caattttggt attacgccaa tagtaggcgt gcgttatagc
tatttatcaa acgctaattt tgcattagct aaagatcgca ttaaagtaaa tccaatatct
gtcaaaacag cctttgctca agttgattta agttatactt atcacttagg cgagttttcc
gttacgccaa ttttgtctgc tcgatatgat acaaatcaag gcagcggaaa aattaatgta
aatcaatatg attttgctta caacgtggaa aaccaacagc aatataacgc agggcttaaa
ttgaaatatc ataatgtgaa attaagtcta ataggcggat taacaaaagc gaaacaagcg
gaaaacaaa aaactgcaga attaaaacta agttttagtt tttaa

FIG. 6D

COMBINATION THERAPY WITH IGA1 PROTEASES

PRIORITY

This application is a continuation of U.S. Ser. No. 10/921,676 filed Aug. 19, 2004, now U.S. Pat. No. 7,407,653, which is a continuation-in-part of CIP of International Application Number PCT/USO4/06615, filed Mar. 5, 2004, which claims priority to U.S. Ser. No. 60/453,055, filed Mar. 7, 2003, the contents of each of which are incorporated herein in their entirety.

GOVERNMENT SUPPORT

This invention was made with government support under grant DE09677 awarded by the National Institutes of Health. The government has certain rights in the invention.

BACKGROUND

Immunoglobulin A1 (IgA1) deposition in human tissues and organs is a characteristic of many human diseases including IgA nephropathy, Dermatitis herpetiformis (DH), and Henoch-Schoenlein purpura (HS). IgA1 deposition is responsible for a variety of clinical manifestations such as renal failure, skin blistering, rash, arthritis, gastrointestinal bleeding and abdominal pain.

There are several available treatment options for patients that present with abnormal IgA1 deposition. These include administration of corticosteroids that have immunosuppressive and anti-inflammatory properties, dietary fish oil supplements that reduce renal inflammation, and angiotensin converting enzyme inhibitors that reduce the risk of progressive renal disease and renal failure. Such treatments do not directly act on IgA1 deposits in tissue or organs.

To address this issue of IgA1 deposit removal, exogenous proteolytic enzymes have been tested in IgA1 deposition animal models (Gesualdo L. et al, (1990) J. Clin. Invest. 86: 715-722 and Nakazawa M. et al. (1986) J. Exp. Med. 164: 1973-1987). The proteases, chymopapain and subtilisin, act by proteolytic cleavage of IgA1 deposits in the kidney but are not specific for IgA1 molecules and will digest a variety of other proteins.

Thus, despite advances in the field, there is a need in the art for therapeutic agents that can be used to treat IgA1 deposition diseases.

SUMMARY OF THE INVENTION

The present invention discloses the use of bacterial IgA1 proteases to treat IgA1 deposition in tissue and organs. Bacterial IgA1 proteases specifically cleave IgA1 molecules and thus provide a means to specifically cleave and remove IgA1 depositions. Accordingly, therapeutic agents for the treatment of diseases characterized by IgA deposition are provided. In particular, therapeutic agents to treat IgA nephropathy, Dermatitis herpetiformis (DH), and Henoch-Schoenlein purpura (HS) are disclosed.

Disclosed herein is a nucleic acid molecule encoding an IgA1 protease that is fused to an amino acid tag located upstream of an IgA1 protease auto-catalytic cleavage site.

In one embodiment, the tag, which is fused to the IgA1 protease, is a tag that specifically binds to a protein ligand, such as an antibody or peptide. The tag can be c-Myc, HA, VSV-G, HSV, FLAG, V5, or HIS.

In one aspect, a pharmaceutical composition for the treatment of IgA1 deposition is provided that comprises an IgA1 protease complexed with an antibody, such as an anti-IgA1 protease antibody.

In another aspect, a pharmaceutical composition for the treatment of IgA1 deposition is provided that comprises a tagged IgA1 protease that is complexed with a ligand of the tag. The tag fused to the IgA1 protease can be c-Myc, HA, VSV-G, HSV, FLAG, V5, or HIS. Accordingly, the ligand can be an anti-tag antibody such as anti-FLAG, anti-MYC, anti-VSV, anti-HA, or anti-V5. Alternatively, the ligand can be a peptide or non-peptide ligand, such as a chelating molecule.

In another aspect, a method for treatment of a disease characterized by IgA1 deposition is provided. The method involves administering to a patient a therapeutically effective amount of an IgA1 protease.

In one embodiment, the method for treatment uses an IgA1 protease fused to a tag complexed with a ligand of the tag, such as an anti-tag antibody. The tag fused to the IgA1 protease can be c-Myc, Flag, HA, VSV-G, HSV, FLAG, V5, or HIS. Accordingly, the anti-tag antibody can be anti-FLAG, anti-MYC, anti-VSV, anti-HA, or anti-V5.

In another embodiment, the disease characterized by IgA1 deposition is IgA nephropathy, Dermatitis herpetiformis, or Henoch-Schoenlein purpura.

BRIEF DESCRIPTION OF THE DRAWINGS

FIG. 5 shows the protein sequence of *Haemophilus influenzae* Rd (SEQ ID NO:4).

FIG. 6 shows the nucleotide sequence of *Haemophilus influenzae* Rd (SEQ ID NO:5).

DETAILED DESCRIPTION

Figure 1:
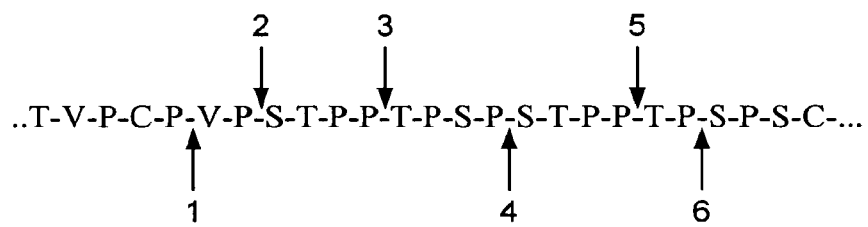
FIG. 1 shows the hinge region of IgA1 and the cleavage sites for several IgA1 proteases within the hinge region (SEQ ID NO:1).

The present invention relates to the use of bacterial Immunoglobulin A1 proteases (IgA1 proteases) to treat diseases that are characterized by IgA1 deposition.

Definitions

As used herein, the term "IgA1 protease" refers to a bacterial enzyme that specifically cleaves human IgA1 molecules. By "specifically cleaves" is meant that the protease cleaves in the hinge region of human IgA1 molecules and generally does not cleave human IgA2 molecules. IgA1 proteases are expressed in gram negative and gram positive bacteria as a single-chain precursor that traverses the bacterial membrane. IgA1 proteases of gram negative bacteria undergo auto-catalytic cleavage releasing an N-terminal soluble IgA1 mature protease. As used herein, "IgA1 protease" also refers to a fragment or portion of a full length IgA1 protease which retains the specific cleavage activity of the full length IgA1 protease.

As used herein, the term "located upstream" refers to the spatial parameter of a tag wherein the amino acid tag sequence is located at least 2 amino acids, or 1, or none, amino-terminal to, and up to 50 amino acids amino-terminal to, the IgA1 protease site of auto-catalytic cleavage such that the tag is located 2, or 1, or none, to 50 amino acids upstream from the carboxyl terminus of the soluble, secreted, IgA1 protease.

As used herein, a "tag" refers to a polypeptide sequence 3 to 40 amino acids in length. A tag can possess a specific binding affinity for a peptide, protein ligand, or a non-peptide ligand. The specific binding affinity permits the IgA1 protease to which it is fused to be complexed with a ligand in order that the IgA1 protease can be detected, isolated, enlarged into a complex form, or used for therapeutic purposes. Herein, a tag also encompasses a fluorescent tag, a luminescent tag, or a chromogenic tag. Non-limiting examples of tags include c-Myc, HA, and VSV-G, HSV, FLAG, V5, and HIS.

By "complexed with a ligand" is meant that the IgA1 protease specifically binds to a binding partner, such as an antibody, or chelating molecule. The specific binding partner can be attached to a matrix, such as a bead. The term "specifically binds" refers to the interaction of two molecules, e.g., an antibody or a protein or peptide or a chelating agent, wherein the interaction is dependent upon the presence of particular structures on the respective molecules. For example, when the two molecules are protein molecules, a structure on the first molecule recognizes and binds to a structure on the second molecule, rather than to proteins in general. "Specific binding", as the term is used herein, means that a molecule binds its specific binding partner with at least 2-fold greater affinity, and preferably at least 10-fold, 20-fold, 50-fold, 100-fold or higher affinity than it binds a non-specific molecule.

By "detected" is meant a manner of determining the presence or absence of the tag, such as "detection" by western blot with anti-tag monoclonal antibody, detection by immunofluorescence, or detection because the tag itself fluoresces. Non-limiting examples of suitable tags according to the invention include c-Myc, Flag, HA, and VSV-G, HSV, FLAG, V5, and HIS.

By "isolated" is meant that the IgA1 protease is separated from bacterial cell materials, such as cell membrane and any protein or nucleic acid present in bacterial growth media. Examples of non-limiting methods of isolation include the isolation of an IgA1 protease that has a poly-Histidine tag using a metal-chelate resin or beads, immunoprecipitation, and affinity column purification using anti-tag antibodies.

As used herein, the term "antibody" refers to an immunoglobulin molecule, or fragment thereof, that is capable of binding antigen, such as a tag or IgA1 protease. The term "antibody" is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a $V_L$ and $V_H$ domain joined by a peptide linker. The scFv's may be covalently or non-covalently linked to form antibodies having two or more binding sites. Thus, antibodies include polyclonal, monoclonal, or other purified preparations of antibodies and recombinant antibodies. Herein, the term "anti-tag antibody" refers to an antibody that specifically binds to a tag.

As used herein, the term "IgA1 deposition" refers to the accumulation of IgA1 immunoglobulin in aggregated or non-aggregated form in human tissue or organs.

Herein, a "disease characterized by IgA1 deposition" refers to any disease in which IgA1 deposition occurs, such as, but not limited to IgA nephropathy, Dermatitis herpetiformis, and Henoch-Schoenlein purpura.

As used herein, "IgA nephropathy" refers to a kidney disease characterized by IgA1 deposits within the kidney.

As used herein, "Dermatitis herpetiformis" refers to a chronic blistering disease associated with deposits of IgA1 in skin and other tissues.

As used herein, "Henoch-Schoenlein purpura" refers to a skin and kidney disease characterized by deposition of IgA1 in skin tissue and kidney tissue.

As used herein, a "pharmaceutical composition" comprises a pharmacologically effective amount of an active agent and a pharmaceutically acceptable carrier. As used herein, "pharmacologically effective amount," or simply "effective amount" refers to that amount of an agent effective to produce the intended pharmacological, therapeutic or preventive result. For example, if a given clinical treatment is considered effective when there is at least a 25% reduction in a measurable parameter associated with a disease or disorder.

I. IgA1 Proteases

Figure 2A:
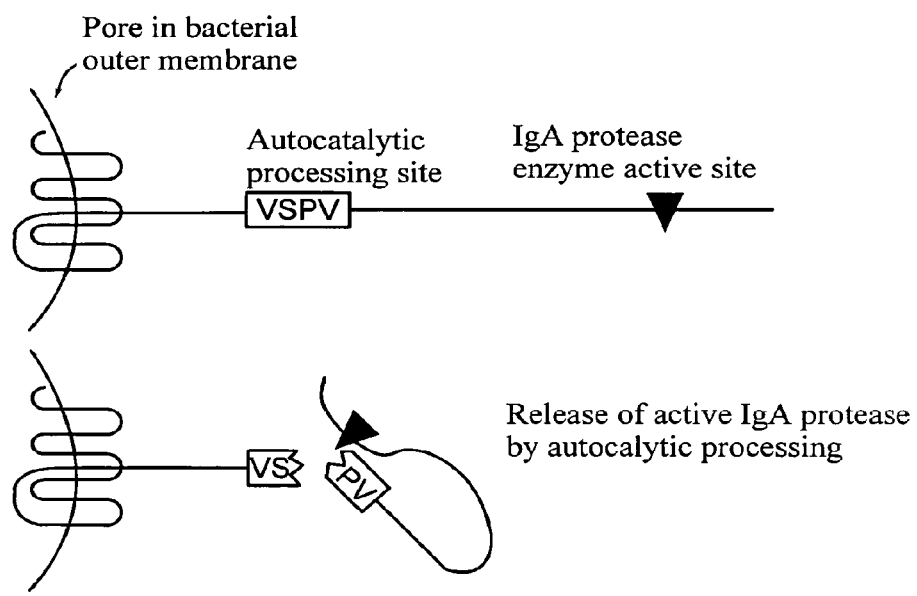
FIG. 2a illustrates the IgA1 protease precursor that undergoes auto-catalytic cleavage and releases a soluble mature IgA1 protease by auto-catalytic cleavage.

Herein, IgA1 proteases are used to treat diseases characterized by IgA1 deposition. IgA1 proteases are bacterial enzymes that specifically cleave human IgA1 molecules. Human IgA2 is resistant to nearly all known IgA1 proteases because IgA2 molecules lack a hinge region that is present in all IgA1 molecules. The hinge region of IgA1 molecules consist of a string of amino acids, that contain cleavage sites for a variety of IgA1 proteases, as illustrated in FIG. 1. IgA1 proteases are expressed in gram-negative bacteria as a single-chain precursor that traverses the inner membrane of bacterium. The precursor protein then inserts itself into the outer bacterial membrane and undergoes auto-catalytic cleavage, releasing a mature soluble IgA1 protease (FIG. 2*a*). IgA proteases of gram-positive bacteria are also useful in this invention, although they do not have an autocatalytic secretion mechanism. For such proteases, an epitope tag may be added into the enzyme protein.

Figure 2B:
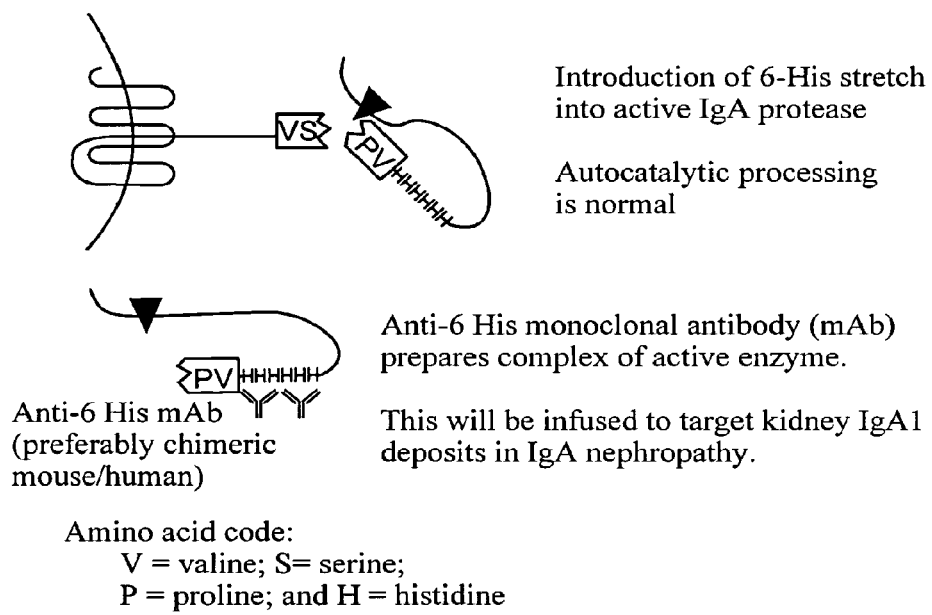
FIG. 2b shows an IgA1 protease wherein a His tag has been fused to the IgA1 protease such that the His tag is located near the carboxyl terminus of the mature IgA1 protease. The soluble IgA1 protease can then be complexed with an anti-His antibody for therapeutic purposes.
Figure 3:
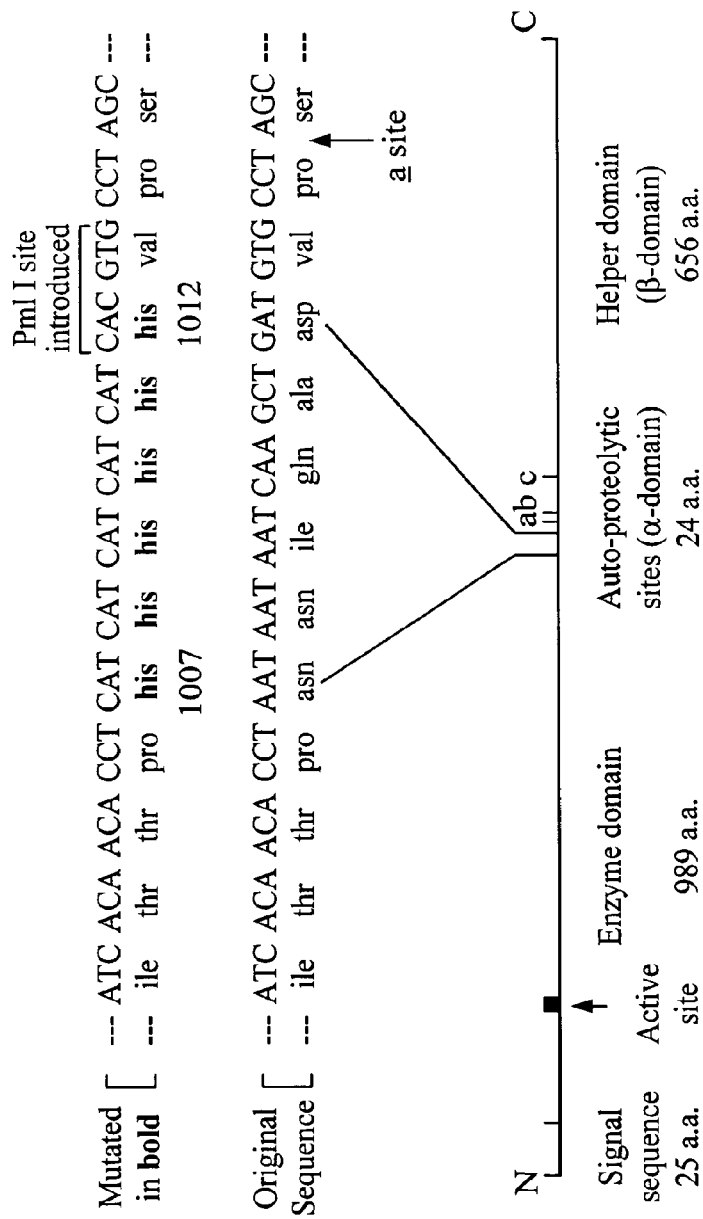
FIG. 3 shows a schematic of the *Haemophilus influenzae* Rd IgA1 protease precursor protein and shows an amino acid sequence that is upstream from the auto-catalytic cleavage site (site a), original sequence (SEQ ID NO:2). The mutated sequence (SEQ ID NO:3) shows where a His tag has been fused in frame to an IgA1 protease, 2 amino acids upstream from the proteolytic cleavage site. The corresponding nucleic acid sequences of the original sequence (SEQ ID NO: 25) and mutated sequence (SEQ ID NO:26) are also shown.

In one embodiment of the present invention a tag sequence is fused in frame to an IgA1 protease, such that the tag sequence is located near the carboxyl terminus of the secreted IgA1 protease (FIG. 2*b*). FIG. 3 shows a schematic of the *Haemophilus influenzae* Rd IgA1 protease precursor protein illustrating that a tag sequence (e.g. His tag) is fused in frame to an IgA1 protease upstream of the auto-catalytic cleavage sites a, b and c.

A variety of bacteria produce IgA1 proteases and are useful in the present invention. These include, but are not limited to *Haemophilus influenzae* type 1 and 2, *Neisseria meningitidis* type 1 and 2, *Nisseria gonorrhoeae, Streptococcus pneumo-* niae, *Streptococcus sanguis, Clostridium ramosum, Prevotella melaminogenica*, and *Ureaplasma ureatyticum*.

The IgA1 protease nucleotide sequences of the present invention can be obtained from any bacteria where an IgA1 protease is expressed, as long as the IgA1 protease is capable of cleaving human IgA1 molecules. Nucleotide sequences encoding IgA1 proteases from numerous bacterial strains have already been identified and include: *Clostridium ramosum* (Genebank Accession, AY028440); *Ureaplasma urealyticum* (Genebank Accession, NC_002162); *Haemophilus influenzae* (Genebank Accession, X59800) and bacterial strains Rd (Genebank Accession, NC-000907), 7768 (Genebank Accession, AF274862), 6338 (Genebank Accession, AF27486), 2509 (Genebank Accession, AF274859), *aegyptius* (Genebank Accession, AF369907), 8625 (Genebank Accession, AJ001741), UK284 (Genebank Accession, X82487), Da66 (Genebank Accession, X82467), HK635 (Genebank Accession, X82488), and other deposited sequences from unidentified strains (Genebank Accession numbers, X59800, X82488, X64357, M87492, M87491, M87490, and M87489); *Neisseria memingitidis* (Genebank Accession number AF235032) and bacterial strains, Z2491 (Genebank Accession, NC-03316), B40 (Genebank Accession, AF012211), Z4099 (Genebank Accession, AF012210), Z4018 (Genebank Accession, AF012209), Z4400 (Genebank Accession, AF012208), Z3524 (Genebank Accession, AF012207), Z4024 (Genebank Accession, AF012206), Z3910 (Genebank Accession, AF012205), Z3906 (Genebank Accession, AF012204), Z2491 (Genebank Accession, AF012203), IHN341 (Genebank Accession, AJ001740), NL3327 (Genebank Accession, AJ001739), NL823 (Genebank Accession, AJ001737), NL3293 (Genebank Accession, AJ001738), HK284 (Genebank Accession, X82487), ETH2 (Genbank Accession, X82469), NGO93 (Genbank Accession, X82482), NCG80 (Genbank Accession, X82479), NG117 (Genbank Accession, X82483), HF96 (Genbank Accession, X82475), HF54 (Genbank Accession, X82473), HF48 (Genbank Accession, X82480), HF13 (Genbank Accession, X82474), NGC65 (Genbank Accession, X82484), NCG16 (Genbank Accession, X82485), SM1894 (Genbank Accession, X82476), EN3771 (Genbank Accession, X82468), NG44/76 (Genbank Accession, X82481), SM1166 (Genbank Accession, X82486), HF159 (Genbank Accession, X82471), 81139 (Genbank Accession, X82477), HF117 (Genbank Accession, X82470), SM1027 (Genbank Accession, X82472) and Genebank Accession number, AF235032; *Nisseria gonorrhoeae* (Genebank Accession number, A12416) and bacterial strain, MS11 (Genebank Accession, S75490); *Streptococcus pneumoniae* (Genebank Accession number, X94909) and bacterial strains MGAS315 (Genebank Accession, NC-004070), R6 (Genebank Accession, NC-003098); and *Streptococcus sanguis* (Genebank Accession, NC-003098) and bacterial strains SK85 (Genebank Accession, Y13461), SK49 (Genebank Accession, Y13460), SK4 (Genebank Accession, Y13459), SK162 (Genebank Accession, Y13458), SK161 (Genebank Accession, Y13457), SK115 (Genebank Accession, Y13456, and Sk112 (Genebank Accession, Y13455). IgA1 proteases of the invention my be utilized as described herein either without or with an attached tag as described hereinbelow.

Vector Construction

In the present invention, sequences encoding IgA1 proteases are cloned into vectors suitable for expression of the protein, such that soluble IgA1 protease can be produced and isolated. The vectors can be constructed using standard methods (Sambrook et al., Molecular Biology: A laboratory Approach, Cold Spring Harbor, N.Y. 1989; Ausubel, et al., Current protocols in Molecular Biology, Greene Publishing, 1995), guided by the principles discussed below. In brief, conventional ligation techniques are used to insert DNA sequences encoding IgA1 protease into a bacterial cloning and/or expression vectors.

To prepare nucleic acids encoding IgA1 protease, a source of genes encoding for IgA1 proteases is required. The genes can be obtained from natural or synthetic sources. Methods for cloning novel IgA1 protease genes from bacterial strains are described in Lomholt H., et al., Mol. Microbiol. (1995) 15(3), 495-508; Fishman, Y. et al., (1985), p. 164-168 in G. K. Schoolink (ed.), The Pathogenic *Neisseria*, Am. Soc. Microbiol., Washington D.C.; Koomey, J. et al., Proc. Natl, Acad. Sci. USA, (1982) 79: 7881-7885; Halter, R, et al., EMBO J., (1984) 3: 1595-1601; Bricker, J. et. al., Proc, Natl. Acad. Sci. USA, (1983), 80:2681-2685; Koomey, J. M. and Falkow, S., supra; Grundy, J. F. et al., J. Bacteriol, (1987) 169:4442-4450; and Gilbert, J. V. et al., Infect. Immun., (1988) 56:1961-1966, all of which are herein incorporated by reference.

Alternatively, DNA encoding a known IgA1 protease can be isolated from bacterial genomic DNA by polymerase chain reaction (PCR) amplification using primers specific for the IgA1 protease gene of interest. Briefly, bacterial genomic DNA is isolated using methods well known in the art, for example using bacterial genomic DNA isolation kits provided by QIAGEN or standard methods described in Sambrook et al., Molecular Biology: A laboratory Approach, Cold Spring Harbor, N.Y. (1989) and Ausubel, et al., Current protocols in Molecular Biology, Greene Publishing, (1995), herein incorporated by reference.

PCR is well known in the art (Mullis and Faloona, Methods Enzymol., (1987), 155: 335, herein incorporated by reference). In general, oligonucleotide primers useful according to the invention are single-stranded DNA or RNA molecules that hybridize selectively to a nucleic acid template that encodes IgA1 protease to prime enzymatic synthesis of a second nucleic acid strand. The primer is complementary to a portion of a target molecule present in a pool of nucleic acid molecules from the bacterial genome. It is contemplated that primers are prepared by synthetic methods, either chemical or enzymatic. Alternatively, such a molecule or a fragment thereof is naturally occurring, and is isolated from its natural source or purchased from a commercial supplier. Mutagenic oligonucleotide primers are 15 to 100 nucleotides in length, ideally from 20 to 40 nucleotides, although oligonucleotides of different length are of use. Preferably, the primers also comprise a unique restriction enzyme sequence.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, Nucleic Acids Res., (1984), 12: 203, incorporated herein by reference. As a result, it is expected that a certain degree of mismatch at the priming site is tolerated. Such mismatch may be small, such as a mono-, di- or tri-nucleotide. Alternatively, it may comprise nucleotide loops, which we define as regions in which mismatch encompasses an uninterrupted series of four or more nucleotides.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence: longer sequences have a higher melting temperature (TM) than do shorter ones, and are less likely to be repeated within a given target sequence, thereby minimizing promiscuous hybridization. Primer sequences with a high G-C content or that comprise palindromic sequences tend to self-hybridise, as do their intended target sites, since unimolecular, rather than bimolecular, hybridization kinetics are generally favored in solution: at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g. formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone.

Primers preferably are designed using computer programs that assist in the generation and optimization of primer sequences. Examples of such programs are "PrimerSelect" of the DNAStar™ software package (DNAStar. Inc.; Madison, Wis.) and OLIGO 4.0 (National Biosciences. Inc.). Once designed, suitable oligonucleotides are prepared by a suitable method, e.g. the phosphoramidite method described by Beaucage and Carruthers (1981) Tetrahedron Lett., 22: 1859) or the triester method according to Matteucci and Caruthers (1981) J. Am. Chem. Soc., 103: 3185, both incorporated herein by reference, or by other chemical methods using either a commercial automated oligonucleotide synthesizer or VLSIPS™ technology.

PCR is performed using template bacterial DNA (at least 1 fg: more usefully, 1-1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer 1 (Perkin-Elmer, Foster City, Calif.), 0.4µ of 1.25 mM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenised, mismatch is required, at least in the first round of synthesis. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above: 1-2 minutes), and extension (72° C. for 1-5 minutes, depending on the length of the amplified product). Final extension is generally for 4 minutes at 72° C., and may be followed by an indefinite (0-24 hour) step at 4° C.

Subsequent to PCR amplification, the DNA can be isolated by standard means, such as gel electrophoresis, or column purification. The DNA encoding the bacterial IgA1 protease can then be digested with appropriate restriction enzymes and ligated into a suitable cloning and/or expression vector.

Vectors and Host Cells

Any vector can be used in the present invention. As used herein, vector refers to a discrete element that is used to introduce heterologous DNA into bacterial cells for the expression and/or replication thereof. Numerous vectors suitable for the present invention are publicly available, including bacterial plasmids and bacteriophage. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding an IgA1 protease according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria. For example, the origin of replication from the plasmid pBR322 is suitable for most Gram-negative bacteria.

Advantageously, a cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors according to the present invention is most conveniently performed in E. coli, an E. coli-selectable marker, for example, the β-lactamase gene that confers resistance to the antibiotic ampicillin, is of use. These can be obtained from E. coli plasmids, such as pBR322 or a pUC plasmid such as pUC18 or pUC19.

Expression vectors usually contain a promoter that is recognized by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence. A preferred promoters of the present invention are the isopropylthiogalactoside (IPTG)-regulatable promoters.

Any bacterial strain is considered a suitable host cell for expression of and cloning of the IgA1 proteases of the present invention. An exemplary host is *E. coli*.

Introduction of Vectors to Host Cells.

Vectors can be introduced to selected host cells by any of a number of suitable methods known to those skilled in the art. For example, vector constructs may be introduced to appropriate bacterial cells by infection using bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y.), but electroporation may also be used (Ausubel et al., Current Protocols in Molecular Biology, (1988), (John Wiley & Sons, Inc., NY, N.Y.)).

Purification of Soluble IgA1 Protease

After introduction of an expression vector encoding IgA1 protease into a suitable bacterial host cell, the bacteria are propagated for the overproduction of soluble IgA1 protease by standard means (Sambrook et al., Molecular Biology: A laboratory Approach, Cold Spring Harbor, N.Y. (1989) and Ausubel, et al., Current protocols in Molecular Biology, Greene Publishing, (1995), herein incorporated by reference). Briefly, bacteria, such as *E. coli*, which harbor an expression vector that encodes IgA1 protease, or bacteria that have DNA encoding IgA1 protease integrated into the bacterial genome, are grown in bacterial growth media at 37° C. When the bacterial cultures reach log phase, soluble IgA1 protease is purified from the growth media by means well known in the art.

For example, *H. influenzae* Rd bacteria that express 6×His-IgA1 protease are cultured as 20 L (two 10 L) in a fermentor charged with brain-heart infusion broth supplemented with NAD and hemin. The cells are grown at 37° C. until they reach stationary phase, 16-20 h. The bacterial mass is then removed with a Pellicon system, and each 10 L of culture supernatant containing the active enzyme is concentrated to 400 ml. The buffers are adjusted to have the protein in 25 mM Tris/HCl buffer, pH 7.5, with 0.05% NaN3. To remove unwanted protein, 80 ml batches of this concentrate is applied to a 40 ml bed-volume DE-52 anion-exchange column equilibrated in 25 mM Tris buffer. IgA protease does not bind to this column, and is collected as flow through using 500 ml Tris buffer. Yield of recovery is typically 85-90% based on assay using human IgA substrate. Ammonium sulfate is then used to precipitate the enzyme (60% saturation ammonium sulfate; 390 gm per L). The precipitate is dissolved with the following buffer: 50 mM sodium phosphate, 12.5 mM Tris/HCl, 0.3 M NaCl and 0.025% sodium azide, adjusted to pH 7.5, and the enzyme is then dialyzed against this buffer for several days. The final volume of enzyme solution is approximately 200 ml for each 10 L of starting culture.

For affinity purification, 40 ml aliquots of the enzyme solution is applied to Ni-NTA-agarose in a column with bed volume of 40 ml. The bound enzyme is washed three times with volumes of 500 ml of buffers containing 50 mM sodium phosphate, 12.5 mM Tris/HCl, 0.3 M NaCl and 0.025% sodium azide. pH of these buffer washes is reduced in stepwise fashion, beginning with pH 7.5, then 6.6, then 6.0, intended to remove weakly adherent, non-enzyme proteins from the nickel ligand. The final wash again uses buffer at pH 7.5, now 200 ml. The 6×His-IgA protease is then eluted from Ni-NTA agarose using 50 ml 0.1 M imidazole in 50 mM Tris/HCl, pH 7.5. The recovered enzyme is concentrated by positive pressure filtration using a 100 kDa cut-off Centricon membrane, washed three times with 25 mM Hepes, pH 7.15, and then stored in Hepes buffer.

Assay for IgA1 Protease Activity

The IgA1 protease is tested for enzyme activity by standard means as described in Plaut, A G and Bachovchin W W, IgA-specific prolyl endopeptidases: serine type. Methods Enzymol. 1994; 244:137-51, herein incorporated by reference. The assay can be performed with purified protease or IgA1 protease present in bacterial growth media. An IgA1 protease has sufficient activity to be useful according to the invention if it has one Unit activity, with Unit equal to one microg human IgA1 cleaved per minute at 37° C.

II. Tagged IgA1 Protease

In one embodiment, the IgA1 protease is fused to a tag, although the invention may be practiced in the absence of a tag and/or ligand complexed thereto. Fusing a tag to the IgA1 proteases of the present invention aids in purification and detection of the protease, as well as provides a means in which the IgA1 protease can form a complex with a ligand, such as an anti-tag antibody, for therapeutic purposes.

To generate an IgA protease comprising a tag, a sequence encoding a tag can be ligated in frame to a sequence encoding an IgA1 protease using conventional molecular biology techniques. The tag sequence is ligated upstream of the DNA sequence encoding the IgA1 protease auto-catalytic cleavage site such that, upon cleavage of the IgA1 protease precursor protein, a soluble IgA1 protease comprising a tag is secreted into bacterial growth media.

Alternatively, an IgA1 protease comprising a tag is generated by PCR-based site directed mutagenesis. There are a number of site-directed mutagenesis methods known in the art which allow one to mutate specific regions within a protein. These methods are embodied in a number of kits available commercially for the performance of site-directed mutagenesis, including both conventional and PCR-based methods. Examples include the EXSITE™ PCR-based site-directed mutagenesis kit available from Stratagene (Catalog No. 200502; PCR based) and the QUIKCHANGE™ site-directed mutagenesis kit from Stratagene (Catalog No. 200518; PCR based), and the CHAMELEON® double-stranded site-directed mutagenesis kit, also from Stratagene (Catalog No. 200509). Briefly, a tag sequence is introduced into a PCR fragment by inclusion of a sequence encoding the tag near the 5' or 3' end of one of the PCR primers. The PCR fragment is generated in a manner to provide appropriate restriction sites such that the fragment can be digested then ligated into parental vector for replacement of specific amino acid codons.

In one embodiment, the tag of the present invention has a specific binding affinity for an antibody, so that the protease forms an immuno-complex upon binding ligand. For example, the tag may comprise a unique epitope for which antibodies are readily available. Alternatively, the tag can comprise metal-chelating amino acids (e.g. His) so that the IgA proteases can complex with a metal-chelating resin or bead, for example nickle-NTA beads.

In another embodiment, the tag comprises a detectable marker, such as an enzyme, or comprises an amino acid that can be labeled with a detectable marker. Detectable markers include, for example, radioisotopes, fluorescent molecules, chromogenic molecules, luminescent molecules, and enzymes. Useful detectable markers in the present invention include biotin for staining with labeled streptavidin conjugate, fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold. Patents teaching the use of such detectable markers include U.S. Pat. Nos. 3,817,837; 3,850,752; 3,939,350; 3,996,345; 4,277,437; 4,275,149; and 4,366,241, the entireties of which are incorporated by reference herein.

Non-limiting examples of suitable tags according to the invention include c-Myc, HA, and VSV-G, HSV, FLAG, V5, and HIS. The amino acid and nucleic acid sequence for each tag is shown below.

Lane (1989) *Antibodies*, Cold Spring Harbor Laboratory, pp. 1-726), herein incorporated by reference.

Assays for detecting tags include, but are not limited to, Western Blot analysis, Immunohistochemistry, Elisa, FACS analysis, enzymatic assays, and autoradiography. Means for performing these assays are well known to those of skill in the art. For example, radiolabels may be detected using photographic film or scintillation counters and fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

| Tag Peptide and Nucleic Acid Sequences | |
|---|---|
| HIS | |
| Protein: HHHHHH | (SEQ ID NO: 6) |
| DNA:     CAC CAT CAC CAT CAC CAT | (SEQ ID NO: 7) |
| | |
| c-Myc | |
| Protein: EQKLISEEDL | (SEQ ID NO: 8) |
| DNA:     GAG CAA AAG CTC ATT TCT GAA GAG GAC TTG | (SEQ ID NO: 9) |
| | |
| HA | |
| Protein: YPYDVPDYA | (SEQ ID NO: 10) |
| DNA:     TAC CCT TAT GAT GTG CCA GAT TAT GCC | (SEQ ID NO: 11) |
| | |
| VSV-G | |
| Protein: YTDIEMNRLGK | (SEQ ID NO: 12) |
| DNA:     TAT ACA GAC ATA GAG ATG AAC CGA CTT GGA AAG | (SEQ ID NO: 13) |
| | |
| HSV | |
| Protein: QPELAPEDPED | (SEQ ID NO: 14) |
| DNA:     CAG CCA GAA CTC GCC CCG GAA GAC CCC GAG GAT | (SEQ ID NO: 15) |
| | |
| V5 | |
| Protein: GKPIPNPLLGLDST | (SEQ ID NO: 16) |
| DNA:     GGC AAA CCA ATC CCA AAC CCA CTG CTG GGC CTG GAT AGT ACT | (SEQ ID NO: 17) |
| | |
| FLAG | |
| Protein: DYKDDDDKG | (SEQ ID NO: 18) |
| DNA:     GAT TAC AAA GAC GAT GAC GAT AAA GGA | (SEQ ID NO: 19) |

Placing a tag on an IgA1 protease has the benefit of enabling easy detection of the IgA1 protease both in vivo and in vitro. A tag that comprises an epitope for an antibody can be detected either using anti-tag antibodies or antibodies that are conjugated to a detectable marker. The detectable marker can be a naturally occurring or non-naturally occurring amino acid that bears, for example, radioisotopes (e.g., $^{125}$I, $^{35}$S), fluorescent or luminescent groups, biotin, haptens, antigens and enzymes. There are many commercially available Abs to tags, such as c-myc, HA, VSV-G, HSV, V5, His, and FLAG. In addition, antibodies to tags used in the invention can be produced using standard methods to produce antibodies, for example, by monoclonal antibody production (Campbell, A. M., *Monoclonal Antibodies Technology: Laboratory Techniques in Biochemistry and Molecular Biology*, Elsevier Science Publishers, Amsterdam, the Netherlands (1984); St. Groth et al., J. Immunology, (1990) 35: 1-21; and Kozbor et al., Immunology Today (1983) 4:72). The anti-tag antibodies can then be detectably labeled through the use of radioisotopes, affinity labels (such as biotin, avidin, etc.), enzymatic labels (such as horseradish peroxidase, alkaline phosphatase, etc) using methods well known in the art, such as described in international application WO 00/70023 and (Harlour and The tag can be further used to isolate the IgA1 protease away from other cellular material. For example, by immunoprecipitation, or by using anti-tag antibody affinity columns or anti-tag antibody conjugated beads. When a HIS tag is used, isolation can be performed using a metal-chelate column (See Hochuli in Genetic Engineering: Principles and Methods ed. J K Setlow, Plenum Press, NY, chp 18, pp 87-96). Means for performing these types of purification are well known in the art.

In a preferred embodiment, an anti-tag antibody is used to generate an IgA1 protease immuno-complex such that the IgA1 protease retains enzymatic activity once complexed. Such an immuno-complex can be used in pharmaceutical preparations for the treatment of IgA1 deposition diseases. For example, an IgA1 immuno-complex, when administered to a patient, is believed to become trapped in the glomerulous of the kidney, a site of IgA1 deposition in IgA nephropathy and Henoch-Schoenlein purpura disease.

III. Treatment of IgA1 Deposition Diseases

Herein, IgA1 proteases are used as therapeutic agents to treat IgA1 deposition diseases. The abnormal deposition of IgA1 molecules is known to cause renal failure, skin blistering, rash, arthritis, gastrointestinal bleeding and abdominal pain.

IgA Nephropathy

In one embodiment, the invention provides a method for treating IgA nephropathy by administering to a patient in need of such treatment an IgA1 protease. IgA nephropathy is a disease of the kidney. The disease is considered to be an immune-complex-mediated glomerulonephritis, which is characterized by granular deposition of IgA1 in the glomerular mesangial areas. Nephropathy results and is defined by proliferative changes in the glomerular mesangial cells.

IgA nephropathy is one of the most common types of chronic glomerulonephritis and a frequent cause of end-stage renal disease.

Dermatitis Herpetiformis

The invention further provides a method for treating Dermatitis herpetiformis (DH) by administering to a patient in need of such treatment an IgA1 protease. Dermatitis herpetiformis is a chronic blistering skin disease associated with deposits of IgA1 at the dermal-epidermal junction (Hall, R P & T. J. Lawley, J. Immunol. (1985) 135(3): 1760-5). DH patients have granular IgA1 deposits and have an associated gluten-sensitive enteropathy (GSE).

Henoch-Schoenlein Purpura

In another embodiment, the invention provides a method for treating Henoch-Schoenlein purpura (HS) by administering to a patient in need of such treatment an IgA1 protease. Henoch-Schoenlein purpura is a skin and kidney disease. HSP is characterized by deposition of IgA1-containing immune complexes in tissue. The disease is diagnosed by observing evidence of IgA1 deposition in the skin tissue or kidney via immunofluorescence microscopy. The clinical manifestations typically include rash; arthralgias; abdominal pain; and renal disease.

Animal Models

The therapeutic effect of IgA proteases of the present invention can be tested in any suitable animal model known to those skilled in the art. Some exemplary animal models are described below.

1. IgA Nephropathy

A number of rat and mice animal models of IgA nephropathy are available and are useful in the present invention. These models are described in Emancipator, S, N. et al., (1987) Animal models of IgA nephropathy In IgA nephropathy. A. R. Clarkson, editor. Martinus Nijhoff publishing, Boston. 188-203, herein incorporated by reference in its entirety. An exemplary model is described in Gesualdo L. et al, (1990) J. Clin. Invest. 86: 715-722, also herein incorporated in its entirety. Briefly, an IgA antibody/dextran sulfate complex is injected into mice. The immuno-complex lodges in the kidney and the mice present with glomerulonephritis that resembles typical cases of human IgA nephropathy. It is preferred that in the above models, human IgA1 is introduced and expressed in the model as described further in the Examples. How the model is made and used for testing therapeutic agents is described in more detail below.

Soluble immune complexes of dextran sulfate (500 kD, Sigma Chemical Co., St. Louis, Mo.) and monoclonal IgA anti-β1-6 glycoside (J558: Litton Bionetics, Kensington, Md.) are prepared at threefold excess (26.5 μg dextran/mg J558 (Nephropathy model); 22.0 μg dextran/mg MOPC 104 E (normal control)). Complexes containing 3 mg antibody are injected into Swiss-Webster mice via tail vein injection. After 1 hour, the point of maximal deposition of IgA complexes in the kidney, mice are injected intraperitoneally with multiple doses of either saline or therapeutic agent at given intervals, such as 10 minute intervals. The mice are killed 1 hour after the last injection.

Kidneys are then isolated from each mouse to look at IgA1 deposition and morphology by light, immunofluorescence, and electron microscopy.

Briefly, to monitor IgA1 deposition, snap-frozen samples of renal cortex, cryostat sectioned at 4 um, are stained with fluoresceinated IgG fractions of goat antisera specific for mouse IgA (US Biochemical Corp) by direct immunofluorescence to semiquantitatively score for IgA1 deposits (Nakazawa, M. et al., (1986) Lab. Invest. 55:551-556, and Nakazawa, M. et al., (1986) J. Exp. Med. 164:1973-1987). A therapeutic agent is regarded as an effective agent when the number of IgA1 deposits scored is reduced towards the number of IgA1 deposits observed in a normal kidney.

Morphological changes, such as expansion of mesangial matrix and mesangial hypercellularity, is scored by staining sections of renal cortex with PAS reagent (Gesualdo, L. et al, (1990) J. Clin. Invest. 86: 715-722). Briefly, renal cortex is fixed in 10% formalin, embedded in paraffin and stained. Expansion of mesangial matrix and mesangial hypercellularity is scored semiquantitatively according to the methods described in Nakazawa, M. et al. (1986) Lab. Invest. 55:551-556, and Nakazawa, M. et al. (1986) J. Exp. Med. 164:1973-1987, herein incorporated by reference in their entirety.

Normal mesangial matrix is scored as 0. Expansion of mesangial matrix is scored as +1 when widened mesangial stalks are observed, +2 when matrix encroachment on capillary lumens is observed, and +3 when conspicuous widening of mesingial stalk is observed along with a decrease in capillary lumen. A therapeutic agent is regarded as effective agent when the expansion of mesangial matrix is reduced towards the morphology of the matrix observed in a normal kidney, for example to a score of +2, or +1, or 0.

Normal mesangial cellularity is scored as 0 and is defined as 3 or fewer cell nuclei per mesengial area. Hypercellularity is scored as +1 when 4 to 6 cell nuclei per mesengial area are observed, as +2 when 4 to 6 cell nuclei per mesengial area are observed in most areas but some areas have 7 or more nuclei, and as +3 when 7 or more cell nuclei per mesengial area are observed in most areas. A therapeutic agent is regarded as effective agent when the mesangial hypercellularity is reduced towards that observed in a normal kidney, for example to a score of +2, or +1, or 0.

Total glomerular area, matrix area, and glomerular cellularity are also quantified in randomly selected glomeruli from each mouse by computer morphometry (Cue image analysis system, Olympus Corp., Columbia, Md.) (Gesualdo L. et al, (1990) J. Clin. Invest. 86: 715-722). Briefly, cubes of cortex are fixed in 2.5% gluteraldehyde in 0.1 M sodium cacodylate, post fixed in 1% $OsO_4$, and embedded in Spurr's epoxy (Polysciences, Inc. Warrington, Pa.). 50-70 nm sections are stained with uranyl acetate and lead hydroxide. Coded grids are examined in a JEOL JEM 100 EX microscope and matrix, cellularity, and immune deposits are semiquantified as described in Nakazawa, M. et al., (1986) J. Exp. Med. 164: 1973-1987, herein incorporated by reference in its entirety.

Hematuria (the presence of red blood cells in urine) and proteinura (the presence of protein in urine) are also a suitable measure of IGA Nephropathy. Briefly, mice are placed in metabolic cages and urine is collected for 24 hours. The urine is then centrifuged and assayed for protein by turbidimetry in 3% sulfalicylic acid and hematuria by microscopy, as described in Nakazawa, M. et al., (1986) J. Exp. Med. 164: 1973-1987, herein incorporated by reference in its entirety. Typically, a normal mouse without IgA nephropathy will have less then three red blood cells per high power field (40×), while mice with IgA nephropathy will have greater than 10 red blood cells per high power field. A reduction in the number of red blood cells per high power field is indicative that the therapeutic agent is effective for IgA nephropathy. Mice are tested for hematuria and proteinura before treatment to determine the reference value indicative of disease. A reduction in the reference value, as compared to the value for hematuria and proteinura obtained before treatment, of 5%, 10%, 30%, 40% preferably 50%, and more preferably greater than 50% after treatment with the therapeutic agent is indicative that the agent is effective for treatment of IgA1 Nephropathy.

IV Dosage, Formulation and Administration

Herein, bacterial IgA proteases are used to treat IgA deposition diseases. The IgA1 protease of the present invention can be used in a composition that is combined with a pharmaceutically acceptable carrier. Such a composition may also contain diluents, fillers, salts, buffers, stabilizers, solubilizers, and other materials well known in the art. In one aspect, the IgA1 protease is complexed with an antibody to form a therapeutic immuno-complex. Such a therapeutic immuno-complex is particularly useful for treatment of diseases characterized by IgA1 deposition in the kidney since the large immuno-complex is believed to lodge in the renal glomerulus upon administration.

In an alternate embodiment, the pharmaceutical formulation may include two or more different IgA proteases, administered together or sequentially, providing a synergistic effect. For example, an IgA protease of *H. influenzae*, a serine-type protease, may be administered with an IgA protease of *Streptococcus sanguis*, an entirely different metal-dependent protease. Such combined or sequential administration of different proteases may be useful because the enzymes may interact with (e.g., bind to) the IgA1 substrate in different ways, thus providing an advantage over single protease administration.

The term "pharmaceutically acceptable" means a nontoxic material that does not interfere with the effectiveness of the biological activity of the active ingredient(s). The characteristics of the carrier will depend on the route of administration. Such carriers include, but are not limited to, saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, tablets may be coated with a material such as glyceryl monostearate or glyceryl distearate, to delay absorption in the gastrointestinal tract.

Pharmaceutically acceptable salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The composition may also contain other agents, which either enhance the activity of the composition, or compliment its activity or use in treatment, or maintain the activity of the therapeutic agent in storage. Such additional factors and/or agents may be included in the composition to produce a synergistic effect or to minimize side effects. Additionally, administration of the composition of the present invention may be administered concurrently with other therapies.

Administration of the therapeutic agent of the present invention can be carried out in a variety of conventional ways, such as oral ingestion, inhalation, topical application or cutaneous, subcutaneous, intraperitoneal, parenteral or intravenous injection.

The compositions containing the therapeutic agent of the present invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier or vehicle.

Modes of administration of the therapeutic agent of the present invention include intravenous, intramuscular, intraperitoneal, intrasternal, subcutaneous and intra-arterial injection and infusion; preferably intravenous injection. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents, and/or compounds to shield the immunogenic determinant of the therapeutic agent. Prevention of the action of microorganisms may be improved by the inclusion of various antibacterial and antifungal agents such as paraben, chlorobutanol, phenol sorbic acid and the like. It may also be desirable to include isotonic agents such as sugars, sodium chloride and the like. Prolonged absorption of an injectable pharmaceutical form may be brought about by the inclusion of agents, such as aluminum monostearate and gelatin, which delay absorption. Injectable depot forms are made by forming microencapsule matrices of the therapeutic agent in biodegradable polymers such as polylactide-polyglycolide, poly(orthoesters) and poly(anhydrides). Depending upon the ratio of therapeutic agent to polymer and the nature of the particular polymer employed, the rate of therapeutic agent release can be controlled. Depot injectable formulations are also prepared by entrapping the therapeutic agent in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose dose or multi-dose containers. Extemporaneous injection solutions and suspensions may be prepared from sterile powders, granules and tablets of the kind previously described.

As used herein, a "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. Generally, a composition will be administered in a single dose in the range of 100 µg-10 mg/kg body weight, preferably in the range of 1 µg-100 µg/kg body weight. This dosage may be repeated daily, weekly, monthly, yearly, or as considered appropriate by the treating physician.

When a therapeutically effective amount of the therapeutic agent of the present invention is administered orally, the composition of the present invention can be in the form of a liquid, the composition contains from about 0.5 to 90% by weight of protein of the present invention, and preferably from about 1 to 50% protein of the present invention.

When a therapeutically effective amount of the therapeutic agent of the present invention is administered by intravenous, cutaneous or subcutaneous injection, the protein will be in the form of a pyrogen-free, parenterally acceptable aqueous solution. The preparation of such parenterally acceptable protein solutions, having due regard to pH, isotonicity, stability, and the like, is within the skill in the art. A preferred composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The composition of the present invention may also contain stabilizers, preservatives, buffers, antioxidants, or other additives known to those of skill in the art.

Topical administration, in which the composition is brought in contact with tissue(s), may be suitable for Dermatitis herpetiformis. By "contacting" is meant not only topical application, but also those modes of delivery that introduce the composition into the tissues, or into the cells of the tissues.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The amount of the therapeutic agent of the present invention in the pharmaceutical composition of the present invention will depend upon the nature and severity of the condition being treated, and on the nature of prior treatments, which the patient has undergone. Ultimately, the attending physician will decide the amount of the therapeutic agent of the present invention with which to treat each individual patient. Initially, the attending physician will administer low doses of the therapeutic agent of the present invention and observe the patient's response. Larger doses of may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the therapeutic agent of the present invention will be in the range of 12 to 72 hours of continuous intravenous administration, at a rate of approximately 30 mg/hour. Ultimately the attending physician will decide on the appropriate duration of intravenous therapy using the pharmaceutical composition of the present invention.

EXAMPLES

Example 1

Construction of Tagged IgA1 Protease

Figure 4:
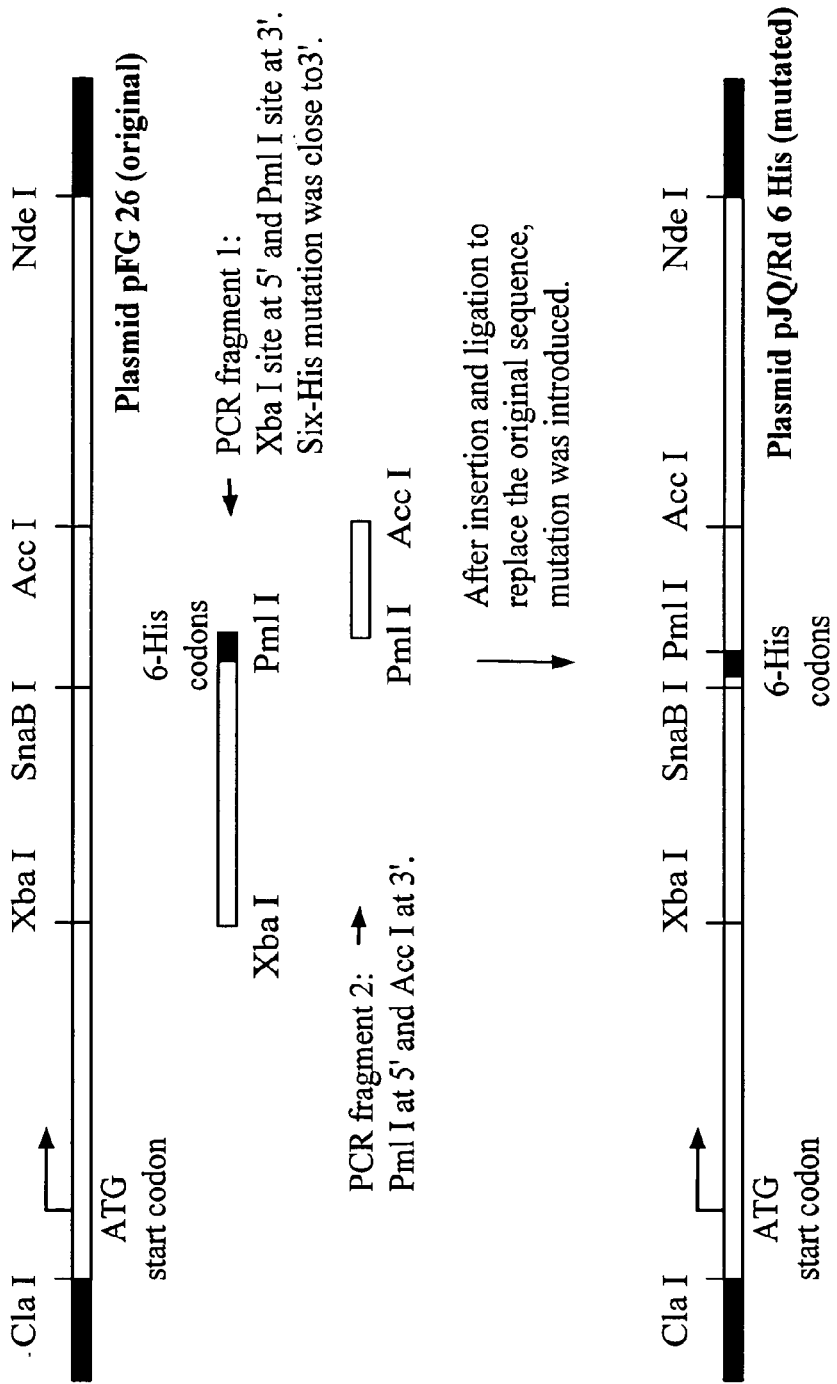
FIG. 4 shows the PCR site directed mutagenesis fragments that were generated for insertion of a HIS tag into *H. influenzae* Rd IgA1 protease by conventional ligation techniques.

A His tag has been fused in frame into *Haemophilus influenzae* IgA1 protease by PCR-based site directed mutagenesis using plasmid pFG26 that contains the DNA sequence encoding *Haemophilus influenzae* IgA1 protease. Two PCR fragments were generated from pFG26 as illustrated in FIG. 4. The first fragment, XbaI and pml 1 fragment, containing the newly inserted HIS tag and pml 1 site was generated using oligonucleotide primers "HFD6His1" (primer 1) and "HFD6His2" (primer 2) shown below. The second fragment, pmL I and Acc I fragment, was generated using primer 3 and primer 4 also shown below.

```
Primer 1: HFD-5 XbaI:

5'GATCCGCTTACCAATTATGC 3'

Primer 2: HFD6His1:

5'-CTTGGTACGCTAGGCACGTGATGATGATGATGATGAGGTGTTGTGAT

ATTTGTCG-3'

Primer 3: HFD6His2:
                                                (SEQ ID NO: 22)
5'-CCTAATAATATTCAAGCTCACGTGCCTAGCGTACC-3'

Primer 4: HFD-F-ACCI:
                                                (SEQ ID NO: 23)
5'-TTCAGCAGAAGTCTCTTGC-3'
```

After amplification of the two fragments by PCR, the fragments were digested with either Xba I and Pml I or Pml I and Acc I and ligated into the Xba I and Acc I sites of the parental pFG26 plasmid using conventional techniques. The mutation was confirmed by DNA sequence and the new plasmid designated pJQ/Rd6His. The fragments were designed such that DNA codons for six Histidines replaced the original codons at position 1007-1012 of the IgA1 protease; asn-asn-ile-gln-ala-asp (SEQ ID NO:24).

Example 2

Generation of a Bacterial Strain that Expresses Tagged IgA1 Protease

A *Haemophilus influenzae* bacterial strain that expresses only a tagged IgA1 protease that is enzymatically active was generated by standard recombination techniques. Briefly, the plasmid pJQ/Rd6His that was generated in Example 1 was cut with restriction enzymes Cla I and Nde I. The gene was isolated and transformed into a *Haemophilus influenzae* bacterial Rd strain (Rd 3-13) that produces an IgA1 protease without enzyme activity (Plaut A G, Qiu, J, Grundy, F. and Wright, A. J Infect Dis. (1992) July; 1 66(1):43-52) to allow for insertion of the His tagged IgA1 protease into the bacterial genome by recombination. The bacteria were then screened for restoration of enzyme activity by testing bacterial growth media of selected colonies for the presence of active protease using human IgA1 as a substrate.

Introduction of the 6-His mutation into the active enzyme was confirmed by verifying the presence of a Pml I site using PCR fragment of the genomic DNA. This strain was designated Rd 6His.

The Rd 6His strain had identical growth rate and colony morphology as did wild type strain Rd. IgA protease activity yield and the size of the enzyme were indistinguishable from wild type. Although the 6 His mutation was introduced just two amino acids away from the auto-proteolytic a site, there was no detectable problem with either the enzyme secretion from the bacterial cell, nor its self-processing.

A monoclonal anti-5His antibody (Qiagen, Inc) bound to the protease as determined by Western blot analysis. When combined with the monoclonal antibody in solution, Rd 6His IgA protease retained full activity.

Example 3

The therapeutic effect of IgA1 protease for the treatment of IgA nephropathy can be tested in a mouse model for IgA nephropathy.

(SEQ ID NO: 20)

(SEQ ID NO: 21)

Mouse Model of IgA Nephropathy

In this model, human IgA1 immunoglobulin is deposited in the mouse glomerular mesangium, and is detected by immunofluorescent analysis using standard immunpathologic methods and three defined antisera. This model shows that injecting these animals with IgA protease decreases IgA deposits.

Description of the Model:

Purification of Polyclonal Human Dimeric IgA1 (dIgA1):

Outdated, pooled blood bank plasma was clotted, and the resulting serum was rendered 50% saturated at room temperature by the addition of solid $(NH_4)_2SO_4$ with stirring. The suspension was kept at 4° C. for 1 h followed by centrifugation at 3000 g for 30 min. The washed precipitate was dissolved in PBS, pH 7.2, dialyzed against this buffer, and then passed through a Sephacryl 300 column. Fractions containing dIgA were pooled. To separate IgA1 from IgA2, this pool was applied to a column of immobilized jacalin in PBS, and dIgA1 was eluted with 0.25M D-galactose in PBS. The dIgA1 was dialyzed against PBS, concentrated, and stored at 4° C. The purity of the dIgA1 was confirmed by SDS-PAGE, reduced and unreduced, and by double diffusion (Ouchterlony) analysis with IgA subclass-specific antisera.

Precipitin Curves to Determine Equivalence:

Goat $F(ab')_2$ anti-human $F(ab')_2$ antibody was purchased from The Jackson Laboratory. Tubes were set up with varying amounts of dIgA1, 0.01 mg-0.4 mg per tube. Each tube received 0.1 mg of goat $F(ab')_2$ anti-human $F(ab')_2$ and then incubated 37° C. for 1 h, and at 4° C. overnight. To obtain the immune precipitates the tubes were centrifuged at 3000 rpm. The precipitates were washed three times in buffer, and after the last rinse the wash buffer was removed and the tubes inverted and allowed to dry. Precipitates were dissolved in 0.1M NaOH and $OD_{280}$ estimated to determine the point of maximum precipitation, the equivalence point.

Immune Complexes (IC) for Injection:

After preliminary animal experiments to decide dosage and time of sacrifice, it was decided to prepare soluble IC at 2-times antigen excess (in our model system IgA1 is the antigen), and to inject complexes containing 800 µg of dIgA1 and 400 µg of goat F(ab')₂ anti-human F(ab')₂ per mouse. Control preparations contained IgA1 plus F(ab')₂ of normal goat IgG.

Injection of Mice:

Six-seven week old Balb/C females obtained from the Charles River VAF facility, were injected intravenously (IV) with IC. After $T_{60min}$ half the animals received an IV injection of 20 ug of IgA1 protease followed by intraperitoneal (IP) injections of 20 ug protease at $T_{66min}$ and $T_{78min}$. The other animals, controls, received IV saline instead of enzyme at the same time intervals. All animals were sacrificed at $T_{120min}$. Kidneys were removed and frozen for cryostat sectioning.

The IgA protease in these initial experiments was a recombinant type 1 enzyme that had been cloned into Rd, the parent strain of *H. influenzae* to produce an enzyme we designated 6HisIgA protease. Approximately 2-3 mg of pure protein was expressed and isolated from this expression system for the preliminary experiments.

Staining of Kidney Sections:

Four uM-thick kidney sections were made in a cryostat and adhered to silane-coated slides. After sections were air-dried they were fixed in acetone for one minute and then frozen at −20° C. until stained. Sections on slides were rehydrated with three-10 min soaks in PBS. Fluorescent antibodies were diluted in PBS containing 1% BSA, and all antibody dilutions were microfuged at 10,000 rpm for 5 min before applying to sections. Dilutions of fluorescein or rhodamine conjugates were applied to rehydrated sections, and the slides were incubated for 90 min in a covered humid chamber. Slides were then washed in PBS, mounted, and randomly numbered. Two readers examined each slide, and independently scored the level of fluorescence. The antibodies used were FITC F(ab')₂ rabbit anti-human IgA (α chain specific), FITC F(ab')₂ rabbit anti-human F(ab')₂, and rhodamine F(ab')₂ rabbit anti-goat F(ab')₂, all purchased from The Jackson Laboratory.

Results:

Fluorescent Antibody Staining of Mesangial IgA1 IC[a]

|  | FITC anti-HuFcα | | FITC anti-Hu(Fab')₂ | | Rhod. anti-goat F(ab')₂ | |
| --- | --- | --- | --- | --- | --- | --- |
|  | saline | enzyme | saline | enzyme | saline | enzyme |
|  | 3 | 2 | 2 | 2 | 2 | 1.5 |
|  | 4 | 2 | 3 | 2 | 3 | 2 |
|  | 4 | 2 | 3 | 2 | 3 | 2 |
|  | 4 | 3 | 3 | 2 | 2.5 | 2 |
|  | 3 | 2 | 3 | 2 | 3 | 2 |
| Group avg. (n = 5/group) | 3.6 | 2.2 | 2.8 | 2.0 | 2.7 | 1.9 |
| Group median (n = 5/group) | 4.0 | 3.0 | 3.0 | 2.0 | 3.0 | 2.0 |
| Exact p-value comparing saline vs. enzyme results | p = .0238 | | p = .0476 | | p = .0397 | |

[a]Six week old Balb/c female mice were injected IV with dIgA1 IC containing polyclonal human IgA1 and goat F(ab')₂ anti-humanF(ab')₂. Beginning one hour later the mice were injected with either IgA protease or saline. After another hour kidneys were removed and 4 um fresh frozen sections cut, fixed, and stained with fluorescent antibodies. Slides were scored in blinded fashion on a scale of 0-4. Five mice received IgA protease and 5 mice (controls) received saline.

Figure 7:
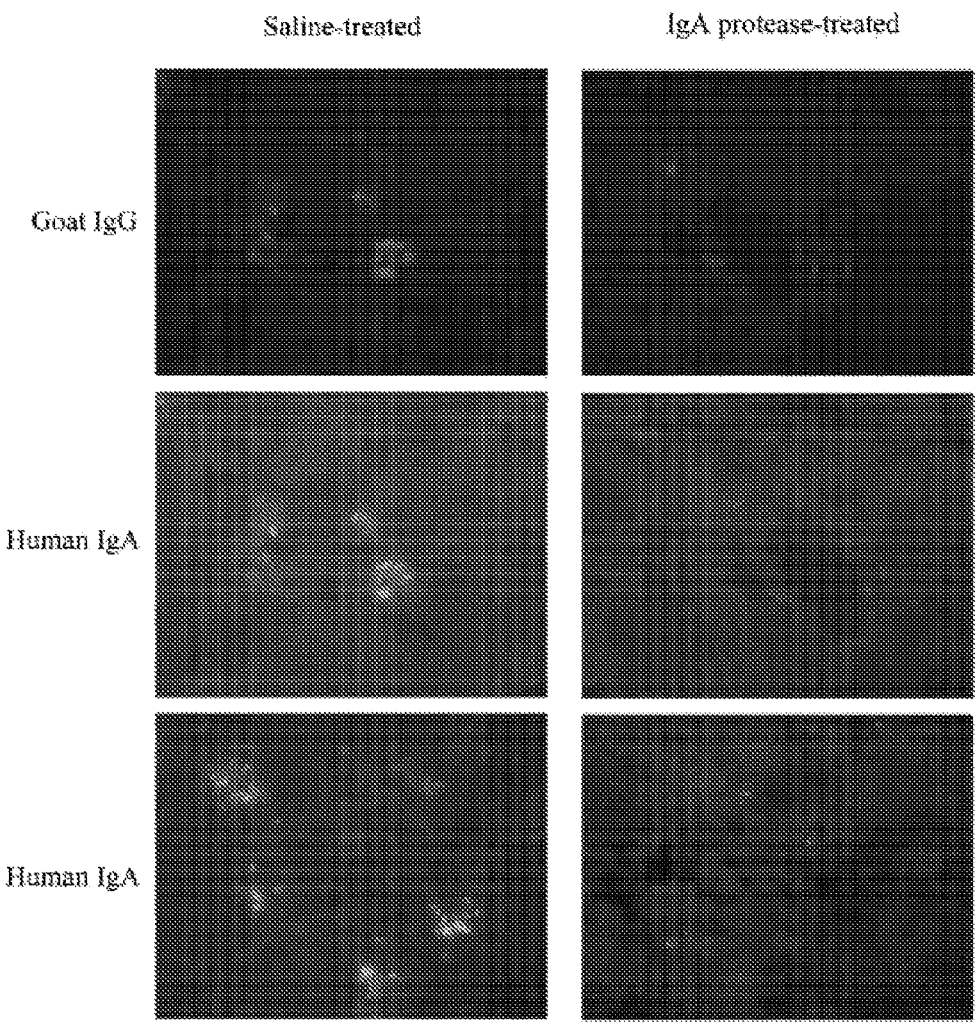
FIG. 7 shows a photomicrograph of mouse kidneys which demonstrates the removal of IC deposition following treatment with IgA1 protease.

Representative photomicrographs of kidney sections are shown in FIG. 7. FIG. 7 shows a photomicrograph of kidneys of mice injected IV 2 hours prior to sacrifice with IC composed of human IgA1 and goat anti-human F(ab')2 and 1 hour prior to sacrifice with IgA1 protease or saline. The right column are from IgA1 protease-treated mice and the left column are form saline-treated controls. The top row (rhodamine fluorescence) shows the goat Ig component of the IC. The middle and bottom rows (fluorescein fluorescence) show the human IgA component. The IgA is detected with anti-human F(ab')2 and anti-human Fc alpha in the middle and bottom rows respectively. As can be seen in the figure, the enzyme has removed most of the deposited IC, both the IgA antigen and the IgG antibody.

Example 4

The therapeutic effect of IgA1 protease for the treatment of Dermatitis herpetiformis can be tested in a mouse model for Dermatitis herpetiformis.

Example 5

The therapeutic effect of IgA1 protease for the treatment of Henoch-Schoenlein purpura can be tested in a mouse model for Henoch-Schoenlein purpura.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. A method comprising a step of administering to an individual having deposits of human IgA1
   (a) an IgA1 protease selected from the group consisting of *Streptococcus pneumoniae* IgA1 protease, *Streptococcus sanguis* IgA1 protease, *Clostridium ramosum* IgA1 protease, *Haemophilus influenzae* IgA1 protease, *Haemophilus aegyptius* IgA1 protease, *Neisseria meningitidis* type 1 and type 2 IgA1 protease, and *Neisseria gonorrhoeae* IgA1 protease and
   (b) another therapy selected from the group consisting of corticosteroids, dietary fish oil supplements, angiotensin converting enzyme inhibitors, and combinations thereof, such that the deposits of IgA1 are reduced.

* * * * *

SEQUENCE LISTING

```
<160> NUMBER OF SEQ ID NOS: 28

<210> SEQ ID NO 1
<211> LENGTH: 25
<212> TYPE: PRT
<213> ORGANISM: Homo sapiens

<400> SEQUENCE: 1

Thr Val Pro Cys Pro Val Pro Ser Thr Pro Pro Thr Pro Ser Pro Ser
1               5                   10                  15

Thr Pro Pro Thr Pro Ser Pro Ser Cys
```

```
            20                  25

<210> SEQ ID NO 2
<211> LENGTH: 13
<212> TYPE: PRT
<213> ORGANISM: Haemophilus influenzae

<400> SEQUENCE: 2

Ile Thr Thr Pro Asn Asn Ile Gln Ala Asp Val Pro Ser
1               5                  10

<210> SEQ ID NO 3
<211> LENGTH: 13
<212> TYPE: PRT
<213> ORGANISM: Artificial Sequence
<220> FEATURE:
<223> OTHER INFORMATION: Mutated Protease Sequence

<400> SEQUENCE: 3

Ile Thr Thr Pro His His His His His His Val Pro Ser
1               5                  10

<210> SEQ ID NO 4
<211> LENGTH: 1694
<212> TYPE: PRT
<213> ORGANISM: Haemophilus influenzae

<400> SEQUENCE: 4

Met Leu Asn Lys Lys Phe Lys Leu Asn Phe Ile Ala Leu Thr Val Ala
1               5                  10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Arg Phe Ser
            35                  40                  45

Val Gly Ala Thr Asn Val Glu Val Arg Asp Lys Asn Asn His Ser Leu
        50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
            100                 105                 110

Leu Asn Gly Asn Met Asn Asn Gly Asn Ala Lys Ser His Arg Asp Val
        115                 120                 125

Ser Ser Glu Glu Asn Arg Tyr Phe Ser Val Glu Lys Asn Glu Tyr Pro
    130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Ser
        195                 200                 205

Gln Phe Ile Tyr Lys Lys Gly Asp Asn Tyr Ser Leu Ile Leu Asn Asn
    210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
```

```
                    245                 250                 255
Leu Ile Gly Phe Gly Asn Ser Lys Glu His Ser Asp Pro Lys Gly
                260                 265                 270

Ile Leu Ser Gln Asp Pro Leu Thr Asn Tyr Ala Val Leu Gly Asp Ser
            275                 280                 285

Gly Ser Pro Leu Phe Val Tyr Asp Arg Glu Lys Gly Lys Trp Leu Phe
        290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Pro Glu Phe Ala Lys Thr Val Leu Asp Lys
                325                 330                 335

Asp Thr Ala Gly Ser Leu Thr Gly Ser Asn Thr Gln Tyr Asn Trp Asn
                340                 345                 350

Pro Thr Gly Lys Thr Ser Val Ile Ser Asn Gly Ser Glu Ser Leu Asn
            355                 360                 365

Val Asp Leu Phe Asp Ser Gln Asp Thr Asp Ser Lys Lys Asn Asn
    370                 375                 380

His Gly Lys Ser Val Thr Leu Arg Gly Ser Gly Thr Leu Thr Leu Asn
385                 390                 395                 400

Asn Asn Ile Asp Gln Gly Ala Gly Gly Leu Phe Phe Glu Gly Asp Tyr
                405                 410                 415

Glu Val Lys Gly Thr Ser Asp Ser Thr Thr Trp Lys Gly Ala Gly Val
                420                 425                 430

Ser Val Ala Asp Gly Lys Thr Val Thr Trp Lys Val His Asn Pro Lys
            435                 440                 445

Ser Asp Arg Leu Ala Lys Ile Gly Lys Gly Thr Leu Ile Val Glu Gly
        450                 455                 460

Lys Gly Glu Asn Lys Gly Ser Leu Lys Val Gly Asp Gly Thr Val Ile
465                 470                 475                 480

Leu Lys Gln Gln Ala Asp Ala Asn Asn Lys Val Lys Ala Phe Ser Gln
                485                 490                 495

Val Gly Ile Val Ser Gly Arg Ser Thr Val Val Leu Asn Asp Asp Lys
            500                 505                 510

Gln Val Asp Pro Asn Ser Ile Tyr Phe Gly Phe Arg Gly Gly Arg Leu
        515                 520                 525

Asp Ala Asn Gly Asn Asn Leu Thr Phe Glu His Ile Arg Asn Ile Asp
    530                 535                 540

Asp Gly Ala Arg Leu Val Asn His Asn Thr Ser Lys Thr Ser Thr Val
545                 550                 555                 560

Thr Ile Thr Gly Glu Ser Leu Ile Thr Asp Pro Asn Thr Ile Thr Pro
                565                 570                 575

Tyr Asn Ile Asp Ala Pro Asp Glu Asp Asn Pro Tyr Ala Phe Arg Arg
                580                 585                 590

Ile Lys Asp Gly Gly Gln Leu Tyr Leu Asn Leu Glu Asn Tyr Thr Tyr
            595                 600                 605

Tyr Ala Leu Arg Lys Gly Ala Ser Thr Arg Ser Glu Leu Pro Lys Asn
        610                 615                 620

Ser Gly Glu Ser Asn Glu Asn Trp Leu Tyr Met Gly Lys Thr Ser Asp
625                 630                 635                 640

Glu Ala Lys Arg Asn Val Met Asn His Ile Asn Asn Glu Arg Met Asn
                645                 650                 655

Gly Phe Asn Gly Tyr Phe Gly Glu Glu Glu Gly Lys Asn Gly Asn
            660                 665                 670
```

-continued

```
Leu Asn Val Thr Phe Lys Gly Lys Ser Glu Gln Asn Arg Phe Leu Leu
        675                 680                 685

Thr Gly Gly Thr Asn Leu Asn Gly Asp Leu Lys Val Glu Lys Gly Thr
    690                 695                 700

Leu Phe Leu Ser Gly Arg Pro Thr Pro His Ala Arg Asp Ile Ala Gly
705                 710                 715                 720

Ile Ser Ser Thr Lys Lys Asp Gln His Phe Ala Glu Asn Asn Glu Val
                725                 730                 735

Val Val Glu Asp Asp Trp Ile Asn Arg Asn Phe Lys Ala Thr Asn Ile
                740                 745                 750

Asn Val Thr Asn Asn Ala Thr Leu Tyr Ser Gly Arg Asn Val Ala Asn
            755                 760                 765

Ile Thr Ser Asn Ile Thr Ala Ser Asp Asn Ala Lys Val His Ile Gly
        770                 775                 780

Tyr Lys Ala Gly Asp Thr Val Cys Val Arg Ser Asp Tyr Thr Gly Tyr
785                 790                 795                 800

Val Thr Cys Thr Thr Asp Lys Leu Ser Asp Lys Ala Leu Asn Ser Phe
                805                 810                 815

Asn Ala Thr Asn Val Ser Gly Asn Val Asn Leu Ser Gly Asn Ala Asn
            820                 825                 830

Phe Val Leu Gly Lys Ala Asn Leu Phe Gly Thr Ile Ser Gly Thr Gly
        835                 840                 845

Asn Ser Gln Val Arg Leu Thr Glu Asn Ser His Trp His Leu Thr Gly
    850                 855                 860

Asp Ser Asn Val Asn Gln Leu Asn Leu Asp Lys Gly His Ile His Leu
865                 870                 875                 880

Asn Ala Gln Asn Asp Ala Asn Lys Val Thr Thr Tyr Asn Thr Leu Thr
                885                 890                 895

Val Asn Ser Leu Ser Gly Asn Gly Ser Phe Tyr Tyr Leu Thr Asp Leu
            900                 905                 910

Ser Asn Lys Gln Gly Asp Lys Val Val Thr Lys Ser Ala Thr Gly
    915                 920                 925

Asn Phe Thr Leu Gln Val Ala Asp Lys Thr Gly Glu Pro Thr Lys Asn
    930                 935                 940

Glu Leu Thr Leu Phe Asp Ala Ser Asn Ala Thr Arg Asn Asn Leu Asn
945                 950                 955                 960

Val Ser Leu Val Gly Asn Thr Val Asp Leu Gly Ala Trp Lys Tyr Lys
                965                 970                 975

Leu Arg Asn Val Asn Gly Arg Tyr Asp Leu Tyr Asn Pro Glu Val Glu
            980                 985                 990

Lys Arg Asn Gln Thr Val Asp Thr Thr Asn Ile Thr Thr Pro Asn Asn
    995                 1000                1005

Ile Gln Ala Asp Val Pro Ser Val Pro Ser Asn Asn Glu Glu Ile
    1010                1015                1020

Ala Arg Val Glu Thr Pro Val Pro Pro Ala Pro Ala Thr Pro
    1025                1030                1035

Ser Glu Thr Thr Glu Thr Val Ala Glu Asn Ser Lys Gln Glu Ser
    1040                1045                1050

Lys Thr Val Glu Lys Asn Glu Gln Asp Ala Thr Glu Thr Thr Ala
    1055                1060                1065

Gln Asn Gly Glu Val Ala Glu Glu Ala Lys Pro Ser Val Lys Ala
    1070                1075                1080

Asn Thr Gln Thr Asn Glu Val Ala Gln Ser Gly Ser Glu Thr Glu
    1085                1090                1095
```

```
Glu Thr Gln Thr Thr Glu Ile Lys Glu Thr Ala Lys Val Glu Lys
    1100                1105                1110
Glu Glu Lys Ala Lys Val Glu Lys Asp Glu Ile Gln Glu Ala Pro
    1115                1120                1125
Gln Met Ala Ser Glu Thr Ser Pro Lys Gln Ala Lys Pro Ala Pro
    1130                1135                1140
Lys Glu Val Ser Thr Asp Thr Lys Val Glu Glu Thr Gln Val Gln
    1145                1150                1155
Ala Gln Pro Gln Thr Gln Ser Thr Thr Val Ala Ala Ala Glu Ala
    1160                1165                1170
Thr Ser Pro Asn Ser Lys Pro Ala Glu Glu Thr Gln Pro Ser Glu
    1175                1180                1185
Lys Thr Asn Ala Glu Pro Val Thr Pro Val Val Ser Lys Asn Gln
    1190                1195                1200
Thr Glu Asn Thr Thr Asp Gln Pro Thr Glu Arg Glu Lys Thr Ala
    1205                1210                1215
Lys Val Glu Thr Glu Lys Thr Gln Glu Pro Pro Gln Val Ala Ser
    1220                1225                1230
Gln Ala Ser Pro Lys Gln Glu Gln Ser Glu Thr Val Gln Pro Gln
    1235                1240                1245
Ala Val Leu Glu Ser Glu Asn Val Pro Thr Val Asn Asn Ala Glu
    1250                1255                1260
Glu Val Gln Ala Gln Leu Gln Thr Gln Thr Ser Ala Thr Val Ser
    1265                1270                1275
Thr Lys Gln Pro Ala Pro Glu Asn Ser Ile Asn Thr Gly Ser Ala
    1280                1285                1290
Thr Ala Ile Thr Glu Thr Ala Glu Lys Ser Asp Lys Pro Gln Thr
    1295                1300                1305
Glu Thr Ala Ala Ser Thr Glu Asp Ala Ser Gln His Lys Ala Asn
    1310                1315                1320
Thr Val Ala Asp Asn Ser Val Ala Asn Asn Ser Glu Ser Ser Asp
    1325                1330                1335
Pro Lys Ser Arg Arg Arg Arg Ser Ile Ser Gln Pro Gln Glu Thr
    1340                1345                1350
Ser Ala Glu Glu Thr Thr Ala Ala Ser Thr Asp Glu Thr Thr Ile
    1355                1360                1365
Ala Asp Asn Ser Lys Arg Ser Lys Pro Asn Arg Arg Ser Arg Arg
    1370                1375                1380
Ser Val Arg Ser Glu Pro Thr Val Thr Asn Gly Ser Asp Arg Ser
    1385                1390                1395
Thr Val Ala Leu Arg Asp Leu Thr Ser Thr Asn Thr Asn Ala Val
    1400                1405                1410
Ile Ser Asp Ala Met Ala Lys Ala Gln Phe Val Ala Leu Asn Val
    1415                1420                1425
Gly Lys Ala Val Ser Gln His Ile Ser Gln Leu Glu Met Asn Asn
    1430                1435                1440
Glu Gly Gln Tyr Asn Val Trp Val Ser Asn Thr Ser Met Asn Glu
    1445                1450                1455
Asn Tyr Ser Ser Ser Gln Tyr Arg Arg Phe Ser Ser Lys Ser Thr
    1460                1465                1470
Gln Thr Gln Leu Gly Trp Asp Gln Thr Ile Ser Asn Asn Val Gln
    1475                1480                1485
Leu Gly Gly Val Phe Thr Tyr Val Arg Asn Ser Asn Asn Phe Asp
```

|  |  | 1490 |  |  |  | 1495 |  |  |  | 1500 |  |

Lys Ala Ser Ser Lys Asn Thr Leu Ala Gln Val Asn Phe Tyr Ser
1505                1510                1515

Lys Tyr Tyr Ala Asp Asn His Trp Tyr Leu Gly Ile Asp Leu Gly
1520                1525                1530

Tyr Gly Lys Phe Gln Ser Asn Leu Lys Thr Asn His Asn Ala Lys
1535                1540                1545

Phe Ala Arg His Thr Ala Gln Phe Gly Leu Thr Ala Gly Lys Ala
1550                1555                1560

Phe Asn Leu Gly Asn Phe Gly Ile Thr Pro Ile Val Gly Val Arg
1565                1570                1575

Tyr Ser Tyr Leu Ser Asn Ala Asn Phe Ala Leu Ala Lys Asp Arg
1580                1585                1590

Ile Lys Val Asn Pro Ile Ser Val Lys Thr Ala Phe Ala Gln Val
1595                1600                1605

Asp Leu Ser Tyr Thr Tyr His Leu Gly Glu Phe Ser Val Thr Pro
1610                1615                1620

Ile Leu Ser Ala Arg Tyr Asp Thr Asn Gln Gly Ser Gly Lys Ile
1625                1630                1635

Asn Val Asn Gln Tyr Asp Phe Ala Tyr Asn Val Glu Asn Gln Gln
1640                1645                1650

Gln Tyr Asn Ala Gly Leu Lys Leu Lys Tyr His Asn Val Lys Leu
1655                1660                1665

Ser Leu Ile Gly Gly Leu Thr Lys Ala Lys Gln Ala Glu Lys Gln
1670                1675                1680

Lys Thr Ala Glu Leu Lys Leu Ser Phe Ser Phe
1685                1690

<210> SEQ ID NO 5
<211> LENGTH: 5085
<212> TYPE: DNA
<213> ORGANISM: Haemophilus influenzae

<400> SEQUENCE: 5
atgctaaata aaaaattcaa actcaatttt attgcgctta ctgtcgccta cgcattaacc      60
ccttatacag aagctgcgtt agtgagagac gatgtggatt atcaaatatt tcgtgatttt     120
gcagaaaata aagggagatt ttctgttggt gcaacaaatg tggaagtgag agataaaaat     180
aaccactctt taggcaatgt tttacctaat ggcattccga tgattgattt tagtgttgtg     240
gatgtagata acgcatcgc cacattgata aatccacaat atgtagtagg tgtaaaacac     300
gttagtaacg gcgtgagtga actacatttt gggaacttaa atggcaatat gaataatggc     360
aatgctaaat cgcaccgaga tgtatcttca gaagaaaata gatatttttc cgttgagaaa     420
aatgagtatc caactaaatt gaatggaaaa gcagtaacta ctgaagatca aactcaaaaa     480
cgccgtgaag actactatat gccacgtctt gataaatttg ttaccgaagt tgcaccaata     540
gaggcttcaa ctgcaagtag tgatgctggc acatataatg atcagaataa atatcctgct     600
tttgtaagac taggaagtgg tagtcaattt atttataaaa aaggagataa ttacagctta     660
attttaaata tcatgaggt tggaggcaat atcttaaat tggtgggcga tgcctatacc     720
tatggtattg caggcacacc ttataaagta aaccacgaaa taatggact aattggtttt     780 ggcaattcaa aagaggaaca cagcgatcca aaaggaatat tatctcaaga tccgcttacc     840
aattatgctg tttaggcga cagtggctcc ccattatttg tatatgatag agaaaaagga     900
aaatggcttt ttcttgggtc ttatgatttt tgggcaggtt ataacaaaaa atcttggcaa     960

```
gaatggaata tttataaacc tgaatttgca aaaactgttc tagataaaga tactgcaggt    1020
tctttaactg gttctaacac ccaatacaat tggaatccta ctggcaaaac aagcgttatt    1080
tctaatggtt ctgaatctct aaatgttgat ttattcgata gtagtcagga tactgactct    1140
aagaagaaca atcacggaaa aagtgtgact cttagaggaa gtggaacgct taccttaaat    1200
aataatatcg atcaaggcgc aggcggcttg ttctttgaag gagattatga agttaaaggc    1260
acttctgata gtaccacttg gaaaggagct ggcgtttctg ttgctgatgg aaaaacagta    1320
acgtggaaag tacataaccc gaaatctgat cgtttagcta aaatcggcaa aggaacatta    1380
attgtagaag gaaagggaga aaataaaggt tcgctaaaag tgggcgatgg tactgttatc    1440
ttaaaacaac aagctgatgc caataataaa gttaaagcct tttcacaagt aggtatagta    1500
agtggtcgct caactgttgt acttaatgat gataagcaag tagatccaaa ttccatttac    1560
tttggcttta gaggtggtcg attagatgcc aatggcaata atctcacttt tgaacatatc    1620
cgtaatattg atgatggcgc aagactagta aatcacaata ccagcaaaac ctctactgta    1680
acaattactg gggaaagtct aattacagat ccaaatacaa ttactccata taatatagac    1740
gcaccagatg aagataatcc ttatgccttt cgacggatta agatggagg acagctctat    1800 ttaaatttgg aaaattacac ttattatgcg ttaagaaaag gtgcgagcac tcgttcagaa    1860
ttacctaaaa atagtggcga aagcaatgaa aattggctat atatgggtaa aacttccgat    1920
gaagccaaaa gaatgtaat gaaccatatc aacaacgagc gtatgaatgg ctttaacggt    1980
tattttggcg aggaagaggg taaaaataac ggtaatctaa atgtgacttt taaaggcaaa    2040
agtgagcaaa atcgcttttt attaacaggc ggaacaaacc ttaatggcga tttaaaggtt    2100
gaaaaaggca cattattcct ttctggcaga ccaacaccgc acgcaagaga tattgcaggt    2160
atttcttcga caaaaaaaga tcaacacttt gctgaaaata tgaagtggt agtagaagat    2220 gactggatta accgcaattt taaagcaaca aatattaatg taaccaataa cgcaacccctt   2280 tattcaggtc gcaatgttgc aaacattact tcaaatatca cagcttctga taatgcaaaa    2340
gtacatattg gctataaagc aggcgatacc gtttgtgtac gttctgacta tacgggctat    2400
gtgacttgca ctactgacaa gttatccgat aaagcccta atagctttaa cgccaccaat    2460
gtatctggca atgtaaattt atcaggtaat gcaaactttg tcttaggcaa agctaactta    2520
ttcggcacaa ttagcggcac gggaaatagc caagtacgtt taaccgaaaa tagccattgg    2580
catttaacag gcgatagcaa tgttaatcag ttaaatttag acaagggcaa tattcattta    2640
aatgcacaaa acgatgcaaa taaagtaact acatataaca cgctgactgt gaatagctta    2700
tcaggtaacg gttcttttcta ttatttaact gatctttcca ataaacaagg cgacaaagtt    2760
gttgtaacta aatccgccac aggtaacttt acattacaag tggcagataa aacaggcgag    2820
cctacaaaaa atgaactcac gctttttgat gcgtcaaatg ctacaagaaa taatttgaat    2880
gtgtcattag ttgggaatac cgttgattta ggtgcttgga aatataaatt acgtaatgtt    2940
aatggacgtt acgatttgta taacccagag gtggaaaaaa gaaatcaaac tgtcgatacg    3000
acaaatatca caacacctaa taatattcaa gctgatgtgc ctagcgtacc aagtaacaat    3060
gaagaaatag cccgtgttga aacaccagtt ccaccacctg cgcctgctac accatcagag    3120
acaactgaaa cagtggctga aaatagtaag caagaaagta aacagtagaa gaaaacgag    3180 caagacgcaa ccgagacaac agctcaaaat ggagaagttg cagaagaagc taaaccaagt    3240
gtaaaagcta atactcaaac aaatgaagtg gctcaaagtg gaagtgaaac cgaggaaact    3300
caaacgactg aaataaaaga aacagctaaa gtagaaaaag aggaaaaggc taaagtagaa    3360
```

```
aaagatgaaa ttcaagaagc acctcaaatg gcttctgaaa cgtctccgaa acaagcaaag    3420
cctgctccta agaagtttc aactgatacg aaagtagaag aaactcaagt tcaagctcaa     3480
ccgcaaacac aatcgacaac tgttgctgcg gcagaggcaa cttcgccaaa cagtaaacca    3540
gcggaagaaa ctcaaccaag tgaaaaaact aacgctgaac ctgtaacgcc tgtagtatca    3600
aaaaatcaaa cagaaaatac gaccgaccaa ccaacagaaa gagagaaaac ggctaaagta    3660
gaaacagaga aaactcaaga acccctcaa gtggcttctc aagcgtctcc gaaacaggaa     3720
cagtctgaaa ctgttcaacc gcaagcagtg cttgaaagtg aaaatgttcc gactgttaat    3780
aatgcagaag aagttcaagc tcaactgcaa acacaaacaa gtgcaacagt aagcactaaa    3840
caacctgcac cagagaattc aataaatact ggatctgcaa ccgcaataac agaaactgct    3900
gaaaaatccg ataaaccaca aacggaaact gcggcttcga ctgaagatgc tagtcagcat    3960
aaagcgaata ctgttgcgga taattctgta gcaaataatt cagaaagcag tgatccaaag    4020
agtagacgta agaagtat tagccagcct caagagactc tgctgaaga acaacagca       4080 gcttctactg acgaaacaac aatagctgat aattcaaaac gcagtaagcc aaatcgtaga    4140
agtagaagaa gtgttcgctc ggaaccaact gttacaaatg gcagcgatcg ttctacagta    4200
gcattgcgcg atctcacaag tacaaacaca aatgcggtaa tttctgatgc aatggcaaaa    4260
gcacaatttg ttgcattaaa tgtggggaaa gcagtttctc aacatattag ccagttagaa    4320
atgaataacg aggggcaata taacgtttgg gtatctaata cttcaatgaa cgaaaattat    4380
tcctcaagtc aatatcgtcg ttttagttct aaaagtacgc aaactcaact tggttgggat    4440
caaacaatct caaacaatgt tcagttaggt ggcgtgttta cttatgttcg caatagtaac    4500
aactttgata aggcaagcag taaaaatact ctagcacaag ttaatttcta ttctaaatat    4560
tatgcggata atcattggta tttgggcatt gatttaggct acggcaagtt ccaaagcaac    4620
ctaaaaacca atcataatgc gaaatttgct cgccatactg cacaatttgg tttaaccgca    4680
ggcaaagcat ttaatcttgg caattttggt attacgccaa tagtaggcgt gcgttatagc    4740
tatttatcaa acgctaattt tgcattagct aaagatcgca ttaaagtaaa tccaatatct    4800
gtcaaaacag cctttgctca agttgattta agttatactt atcacttagg cgagttttcc    4860
gttacgccaa ttttgtctgc tcgatatgat acaaatcaag gcagcggaaa attaatgta    4920 aatcaatatg attttgctta caacgtggaa aaccaacagc aatataacgc agggcttaaa    4980
ttgaaatatc ataatgtgaa attaagtcta ataggcggat taacaaaagc gaaacaagcg    5040
gaaaaacaaa aaactgcaga attaaaacta agttttagtt tttaa                   5085
```

<210> SEQ ID NO 6
<211> LENGTH: 6
<212> TYPE: PRT
<213> ORGANISM: Artificial Sequence
<220> FEATURE:
<223> OTHER INFORMATION: Heterologous peptide tag sequence

<400> SEQUENCE: 6

His His His His His His
1               5

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide encoding heterologous peptide
      tag sequence

```
<400> SEQUENCE: 7
caccatcacc atcaccat                                                18

<210> SEQ ID NO 8
<211> LENGTH: 10
<212> TYPE: PRT
<213> ORGANISM: Artificial Sequence
<220> FEATURE:
<223> OTHER INFORMATION: Heterologous peptide tag sequence

<400> SEQUENCE: 8

Glu Gln Lys Leu Ile Ser Glu Glu Asp Leu
1               5                   10

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide encoding heterologous peptide
      tag sequence

<400> SEQUENCE: 9
gagcaaaagc tcatttctga agaggacttg                                   30

<210> SEQ ID NO 10
<211> LENGTH: 9
<212> TYPE: PRT
<213> ORGANISM: Artificial Sequence
<220> FEATURE:
<223> OTHER INFORMATION: Heterologous peptide tag sequence

<400> SEQUENCE: 10

Tyr Pro Tyr Asp Val Pro Asp Tyr Ala
1               5

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide encoding heterologous peptide
      tag sequence

<400> SEQUENCE: 11 taccottatg atgtgccaga ttatgcc                                      27

<210> SEQ ID NO 12
<211> LENGTH: 11
<212> TYPE: PRT
<213> ORGANISM: Artificial Sequence
<220> FEATURE:
<223> OTHER INFORMATION: Heterologous peptide tag sequence

<400> SEQUENCE: 12

Tyr Thr Asp Ile Glu Met Asn Arg Leu Gly Lys
1               5                   10

<210> SEQ ID NO 13
<211> LENGTH: 33
<212> TYPE: DNA
<213> ORGANISM: Artificial Sequence
<220> FEATURE:
<223> OTHER INFORMATION: Oligonucleotide encoding heterologous peptide
      tag sequence

<400> SEQUENCE: 13
```
tatacagaca tagagatgaa ccgacttgga aag                                    33

<210> SEQ ID NO 14
<211> LENGTH: 11
<212> TYPE: PRT
<213> ORGANISM: Artificial Sequence
<220> FEATURE:
<223> OTHER INFORMATION: Heterologous peptide tag sequence

<400> SEQUENCE: 14

Gln Pro Glu Leu Ala Pro Glu Asp Pro Glu Asp
1               5                   10

<210> SEQ ID NO 15
<211> LENGTH: 33
<212> TYPE: DNA
<213> ORGANISM: Artificial Sequence
<220> FEATURE:
<223> OTHER INFORMATION: Oligonucleotide encoding heterologous peptide
      tag sequence

<400> SEQUENCE: 15
cagccagaac tcgccccgga agaccccgag gat                                    33

<210> SEQ ID NO 16
<211> LENGTH: 14
<212> TYPE: PRT
<213> ORGANISM: Artificial Sequence
<220> FEATURE:
<223> OTHER INFORMATION: Heterologous peptide tag sequence

<400> SEQUENCE: 16

Gly Lys Pro Ile Pro Asn Pro Leu Leu Gly Leu Asp Ser Thr
1               5                   10

<210> SEQ ID NO 17
<211> LENGTH: 42
<212> TYPE: DNA
<213> ORGANISM: Artificial Sequence
<220> FEATURE:
<223> OTHER INFORMATION: Oligonucleotide encoding heterologous peptide
      tag sequence

<400> SEQUENCE: 17
ggcaaaccaa tcccaaaccc actgctgggc ctggatagta ct                          42

<210> SEQ ID NO 18
<211> LENGTH: 9
<212> TYPE: PRT
<213> ORGANISM: Artificial Sequence
<220> FEATURE:
<223> OTHER INFORMATION: Heterologous peptide tag sequence

<400> SEQUENCE: 18

Asp Tyr Lys Asp Asp Asp Asp Lys Gly
1               5

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide encoding heterologous peptide
      tag sequence

<400> SEQUENCE: 19
gattacaaag acgatgacga taaagga                                           27

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide for site directed mutagenesis

<400> SEQUENCE: 20
gatccgctta ccaattatgc                                                    20

<210> SEQ ID NO 21
<211> LENGTH: 55
<212> TYPE: DNA
<213> ORGANISM: Artificial Sequence
<220> FEATURE:
<223> OTHER INFORMATION: Synthetic oligonucleotide for site directed mutagenesis

<400> SEQUENCE: 21
cttggtacgc taggcacgtg atgatgatga tgatgaggtg ttgtgatatt tgtcg            55

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide for site directed mutagenesis

<400> SEQUENCE: 22
cctaataata ttcaagctca cgtgcctagc gtac                                    34

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide for site directed mutagenesis

<400> SEQUENCE: 23
ttcagcagaa gtctcttgc                                                     19

<210> SEQ ID NO 24
<211> LENGTH: 6
<212> TYPE: PRT
<213> ORGANISM: Haemophilus influenzae

<400> SEQUENCE: 24

Asn Asn Ile Gln Ala Asp
1               5

<210> SEQ ID NO 25
<211> LENGTH: 39
<212> TYPE: DNA
<213> ORGANISM: Artificial Sequence
<220> FEATURE:
<223> OTHER INFORMATION: Oligonucleotide encoding heterologous peptide tag sequence

<400> SEQUENCE: 25
atcacaacac ctaataatat tcaagctgat gtgcctagc                               39

<210> SEQ ID NO 26
<211> LENGTH: 39

```
<212> TYPE: DNA
<213> ORGANISM: Haemophilus influenzae

<400> SEQUENCE: 26
atcacaacac ctcatcatca tcatcatcac gtgcctagc                              39

<210> SEQ ID NO 27
<211> LENGTH: 4
<212> TYPE: PRT
<213> ORGANISM: Homo sapiens

<400> SEQUENCE: 27

Val Ser Pro Val
1

<210> SEQ ID NO 28
<211> LENGTH: 6
<212> TYPE: PRT
<213> ORGANISM: Homo sapiens

<400> SEQUENCE: 28

His His His His His His
1               5
```